United States Patent [19]

Kim et al.

[11] Patent Number: 5,409,933
[45] Date of Patent: Apr. 25, 1995

[54] QUINOLINE DERIVATIVES AND PROCESSES FOR PREPARING THE SAME

[76] Inventors: Wan J. Kim, 383-7, Doryong-dong Yuseong-ku, Daejeon 305-606; Tae S. Lee, Samchang Apt. 1-203, 26-1, Gajang-dong, Seo-ku, Daejeon 302-181; Myung H. Park, Hyundae Apt. 91-107, 482 Apkujeong-dong, Kangnam-ku, Seoul 135-110; Jae D. Ha, Hanbit Apt. 138-708,99 Ayeun-dong, Yuseong-ku, Daejeon 305-333; Bong J. Kim, Hanwool Apt. 101-903, Singseong-dong, Yuseong-ku, Daejeon 305-343; Keun S. Nam, Hanbit Apt. 120-306,99 Ayeun-dong, Yuseong-ku, Daejeon 305-333; Jae Y. Kong, Kongdong Apt. 6-503, 431 Doryong-dong, Yuseong-ku, Daejeon 305-606, all of Rep. of Korea

[21] Appl. No.: 73,207

[22] Filed: Jun. 8, 1993

[51] Int. Cl.⁶ ............... A61K 31/495; A61K 31/47; C07D 401/00; C07D 215/20
[52] U.S. Cl. ..................... 514/254; 514/312; 544/363; 546/156
[58] Field of Search ........... 544/363; 546/156; 514/254, 312

[56] References Cited

U.S. PATENT DOCUMENTS

| | | | |
|---|---|---|---|
| 4,659,734 | 4/1987 | Enomoto et al. | 544/361 |
| 4,981,966 | 1/1991 | Hermecz et al. | 544/363 |
| 4,997,943 | 3/1991 | Iwata et al. | 544/363 |
| 5,164,392 | 11/1992 | Matsumoto et al. | 544/363 |
| 5,217,972 | 6/1993 | Grohe et al. | 544/363 |
| 5,225,413 | 7/1993 | Naik et al. | 544/363 |
| 5,245,037 | 9/1993 | Kuramoto et al. | 544/363 |
| 5,256,662 | 10/1993 | Domagala et al. | 544/363 |
| 5,262,417 | 11/1993 | Gammill et al. | 544/363 |
| 5,281,596 | 1/1994 | Kitao et al. | 544/363 |

FOREIGN PATENT DOCUMENTS

| | | | |
|---|---|---|---|
| 375658 | 6/1990 | European Pat. Off. | 544/363 |
| 6128764 | 10/1981 | Japan | 544/363 |
| 3284171 | 11/1988 | Japan | 544/363 |
| 1019069 | 1/1989 | Japan | 544/363 |

OTHER PUBLICATIONS

Chem. Abst. 116:214316 (1992).
Chem. Abst. 116:151528 (1991).
Chem Abst. 106:18619 (1986).

*Primary Examiner*—Cecilia Tsang
*Attorney, Agent, or Firm*—Kenyon & Kenyon

[57] ABSTRACT

The present invention relates to novel quinoline derivatives of formula (I):

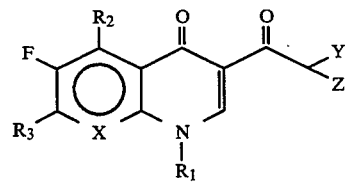

wherein $R_1$, $R_2$, $R_3$, X, Y and Z are defined as in the specification, and pharmaceutically acceptable acid addition salts thereof, and also to processes for preparing these compounds.

The present invention also provides an antibacterial composition comprising a compound of formula (I) or its acid addition salt as an active ingredient and pharmaceutically acceptable excipient.

The novel quinoline derivatives of the present invention have an excellent antibacterial activity against bacteria or bacteroides.

5 Claims, No Drawings

QUINOLINE DERIVATIVES AND PROCESSES FOR PREPARING THE SAME

FIELD OF THE INVENTION

The present invention relates to novel quinoline derivatives and pharmaceutically acceptable acid addition salts thereof which possess a broad spectrum of potent antibacterial activities and are useful as human or veterinary medicaments, and to processes for preparing such compounds.

The present invention also relates to antibacterial compositions containing one or more these compounds as active ingredients.

DESCRIPTION OF THE PRIOR ART

A number of quinolone compounds having a pyridone carboxylic acid as a basic skeleton have been developed, and these compounds have mainly been developed to have a potent and broad spectrum of antibacterial activities.

Among these quinolone derivatives, norfloxacin (Japanese Patent Application Laid-Open No. 141286/1978), enoxacin (Japanese Patent Application Laid-Open No. 310421/1980), ofloxacin (Japanese Patent Application Laid-Open No. 469861/1982), ciprofloxacin (Japanese Patent Application Laid-Open No. 76667/1983) and the like have been on the market. Tosufloxacin and the like recently has become commercially available.

All of these prior art compounds have a carboxy group at the C-3 position of the quinolone nucleus and this type of quinolone antibacterial compounds are crowded in the art. Thus, the development of another type of quinolone antibacterial compounds having a different skeleton is still needed.

SUMMARY OF THE INVENTION

The present invention is concerned with novel quinoline derivatives and their pharmaceutically acceptable acid addition salts, antibacterial compositions containing such compounds, and with processes for preparing such compounds.

DETAILED DESCRIPTION OF THE INVENTION

An object of the present invention is to provide novel quinoline derivatives and their pharmaceutically acceptable acid addition salts having antibacterial activity and also to provide processes for preparing these compounds.

Another object of the present invention is to provide antibacterial compositions containing one or more these compounds as active ingredients.

The present invention provides novel quinoline derivatives represented by the formula (I)

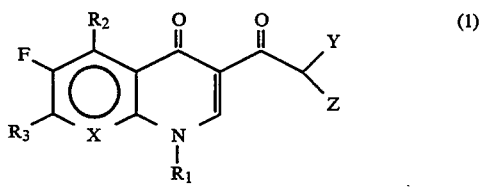

wherein:

$R_1$ is a straight chain or cyclic lower alkyl group having to 1 to 3 carbon atoms, a straight chain or cyclic lower alkyl group having 1 to 3 carbon atoms which is substituted with a halogen atom, a phenyl group or a phenyl group substituted with one or two halogen atoms;

$R_2$ is a hydrogen atom, a lower alkyl or amino group;

$R_3$ is a halogen atom or a substituted or unsubstituted heterocyclic group represented by the following formula (A) which contains at least one nitrogen atom as a hetero atom in the ring;

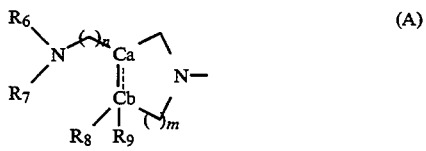

wherein:

$R_6$, $R_7$, $R_8$ and $R_9$ are each hydrogen atoms or lower alkyl groups, or two of these groups may form a bond, m and n are 0 or 1, and $C_a$–$C_b$ may not form a bond, or is a single or double bond;

X is nitrogen atom or C—$R_4$ wherein $R_4$ is hydrogen or halogen atom, or lower alkyl or lower alkoxy group; and Y and Z are each hydrogen atoms, or electron withdrawing groups, for example, ester, cyano, nitro, acyl or substituted acyl, substituted or unsubstituted amide, lower alkylsulfoxy or lower alkylsulfonyl group, and pharmaceutically acceptable acid addition salts thereof.

The present invention also provides an antibacterial compositions which contain compounds represented by the formula (I) as active ingredients.

The present invention is further illustrated hereinbelow.

The novel quinoline derivatives of the present invention can be represented by the formula (I) above. These compounds exhibit antibacterial activity, particularly against bacteria or bacteroides. Therefore, the compounds of the present invention are useful in the prophylaxis and therapy for local or systemic infection caused by the above pathogens.

The present invention also includes pharmaceutically acceptable acid addition salts of the compounds represented by the above formula (I).

Pharmaceutically acceptable salts include inorganic salts such as hydrochloride, sulfate, nitrate and the like, and organic salts such as lactate, ascorbate, maleate, malonate, glutamate, citrate, fumarate, p-toluate, succinate, methanesulfonate and the like.

Preferred compounds of the present invention are those wherein $R_1$ is an ethyl, cyclopropyl, 2-fluoroethyl or 2,4-difluorophenyl group, and $R_3$ is a substituted or unsubstituted piperazine, 3-aminopyrrolidine, 3-aminomethylpyrrolidine, 3-aminomethyl-2,5-dihydropyrrole,

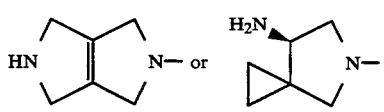

group.

The typical representatives of the compounds represented by the above formula (I) according to the present invention are as follows:

1-cyclopropyl-6-fluoro-7-(piperazin-1-yl)-3-(2-nitroacetyl)-1,4-dihydro-4-oxoquinoline hydrochloride;

1-cyclopropyl-6-fluoro-7-(piperazin-1-yl)-3-(2-nitroacetyl)-1,4-dihydro-4-oxoquinoline trifluoroacetate;

1-cyclopropyl-6,8-difluoro-7-(piperazin-1-yl)-3-(2-nitroacetyl)-1,4-dihydro-4-oxoquinoline hydrochloride;

1-cyclopropyl-6,8-difluoro-7-(3-methylpiperazin-1-yl)-3-(2-nitroacetyl)-1,4-dihydro-4-oxoquinoline hydrochloride;

1-(2,4-difluorophenyl)-6-fluoro-7-(3-aminopyrrolidin-1-yl)-3-(2-nitroacetyl)-1,4-dihydro-4-oxo-1,8-naphthyridine hydrochloride;

1-(2,4-difluorophenyl)-6-fluoro-7-(3-aminopyrrolidin-1-yl)-3-(2-nitroacetyl)-1,4-dihydro-4-oxoquinoline hydrochloride;

1-(2,4-difluorophenyl)-6-fluoro-7-(3-methylpiperazin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2-nitroacetyl)-1,4-dihydro-4-oxoquinoline hydrochloride;

1-cyclopropyl-6-fluoro-8-chloro-7-(3-3R-aminopyrrolidin-1-yl)-3-(2-nitroacetyl)-1,4-dihydro-4-oxoquinoline hydrochloride;

1-cyclopropyl-6-fluoro-8-chloro-7-(3-3S-aminopyrrolidin-1-yl)-3-(2-nitroacetyl)-1,4-dihydro-4-oxoquinoline hydrochloride;

1-cyclopropyl-5-amino-6,8-difluoro-7-(3,5-cis-dimethylpiperazin-1-yl)-3-(2-nitroacetyl)-1,4-dihydro-4-oxoquinoline hydrochloride;

1-cyclopropyl-6,8-difluoro-7-(3-methylaminomethyl-2,5-dihydropyrrol-1-yl)-3-(2-nitroacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-nitroacetyl)-1,4-dihydro-4-oxoquinoline hydrochloride;

1-cyclopropyl-6-fluoro-7-(piperazin-1-yl)-3-(2,2-diethoxycarbonylacetyl)-1,4-dihydro-4-oxoquinoline hydrochloride;

1-cyclopropyl-6-fluoro-7-(piperazin-1-yl)-3-(2-ethoxycarbonylacetyl)-1,4-dihydro-4-oxoquinoline hydrochloride;

1-cyclopropyl-6,8-difluoro-7-(3-aminopyrrolidin-1-yl)-3-(2,2-diethoxycarbonylacetyl)-1,4-dihydro-4-oxoquinoline hydrochloride;

1-cyclopropyl-6,8-difluoro-7-(3-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-3S-methylaminopyrrolidin-1-yl)-3-(2-nitroacetyl)-1,4-dihydro-4-oxoquinoline hydrochloride;

1-cyclopropyl-6-fluoro-8-chloro-7-(3-3R-methylaminopyrrolidin-1-yl)-3-(2-nitroacetyl)-1,4-dihydro-4-oxoquinoline hydrochloride;

1-cyclopropyl-6-fluoro-8-chloro-7-(3-methylaminopyrrolidin-1-yl)-3-(2-nitroacetyl)-1,4-dihydro-4-oxoquinoline hydrochloride;

1-cyclopropyl-6-fluoro-8-methoxy-7-(3-3S-methylaminopyrrolidin-1-yl)-3-(2-nitroacetyl)-1,4-dihydro-4-oxoquinoline hydrochloride;

1-cyclopropyl-6-fluoro-8-methoxy-7-(3-3R-methylaminopyrrolidin-1-yl)-3-(2-nitroacetyl)-1,4-dihydro-4-oxoquinoline hydrochloride;

1-cyclopropyl-6-fluoro-8-methoxy-7-(3-methylaminopyrrolidin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-3R-aminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-3S-aminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-3R-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-3S-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2,2-diethoxycarbonylacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-ethoxycarbonylacetyl)-1,4-dihydro-4-oxoquinoline hydrochloride;

1-ethyl-6,8-difluoro-7-(3-aminopyrrolidin-1-yl)-3-(2-nitroacetyl)-1,4-dihydro-4-oxoquinoline hydrochloride;

1-cyclopropyl-6-fluoro-8-chloro-7-(3-3S-methylaminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-3R-methylaminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-methylaminopyrrolidin-1-yl)-3-(2,2-diethoxycarbonylacetyl)-1,4-dihydro-4-oxoquinoline hydrochloride;

1-cyclopropyl-6-fluoro-8-methoxy-7-(3-3S-methylaminopyrrolidin-1-yl)-3-(2,2-diethoxycarbonylacetyl)-1,4-dihydro-4-oxoquinoline hydrochloride;

1-cyclopropyl-6-fluoro-8-methoxy-7-(3-3R-methylaminopyrrolidin-1-yl)-3-(2,2-diethoxycarbonylacetyl)-1,4-dihydro-4-oxoquinoline hydrochloride;

1-cyclopropyl-6-fluoro-8-methoxy-7-(3-methylaminopyrrolidin-1-yl)-3-(2,2-diethoxycarbonylacetyl)-1,4-dihydro-4-oxoquinoline hydrochloride;

1-(2-fluoroethyl)-6,8-difluoro-7-(3-aminopyrrolidin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2-methanesulfonylacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2-nitroacetyl)-1,4-dihydro-4-oxoquinoline hydrochloride;

1-cyclopropyl-6-fluoro-8-chloro-7-(7-amino-5-azaspiro[2.4]hept-5-yl)-3-(2-nitroacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2,2-diethoxycarbonylacetyl)-1,4-dihydro-4-oxoquinoline hydrochloride;

1-cyclopropyl-6-fluoro-8-chloro-7-(3-aminopyrrolidin-1-yl)-3-(2-acetoacetyl)-1,4-dihydro-4-oxoquinoline hydrochloride;

1-cyclopropyl-6-fluoro-8-chloro-7-(3-aminopyrrolidin-1-yl)-3-(2-trifluoroacetoacetyl)-1,4-dihydro-4-oxoquinoline hydrochloride;

1-cyclopropyl-6-fluoro-8-chloro-7-(3-aminopyrrolidin-1-yl)-3-(2-cyano-2-ethoxycarbonylacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-cyano-2-ethoxycarbonylacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2cyano-2-ethoxycarbonylacetyl)-1,4-dihydro-4-oxoquinoline hydrochloride;

1-cyclopropyl-6-fluoro-8-chloro-7-(3-aminopyrrolidin-1-yl)-3-(2-cyanoacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-cyanoacetyl)-1,4-dihydro-4-oxoquinoline hydrochloride;

1-cyclopropyl-6-fluoro-8-chloro-7-(3, 7-diazabicyclo[3.3.0]oct-1,5-en-3-yl)-3-(2-cyanoacetyl)-1,4-dihydro-4-oxoquinoline hydrochloride;

1-cyclopropyl-6-fluoro-8-chloro-7-(3-aminopyrrolidin-1-yl)-3-(2,2-dicyanoacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-methanesulfonylacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2-methanesulfonylacetyl)-1,4-dihydro-4-oxoquinoline hydrochloride;

1-cyclopropyl-6-fluoro-8-chloro-7-(3-aminopyrrolidin-1-yl)-3-(2,2-diacetoacetyl)-1,4-dihydro-4-oxoquinoline hydrochloride;

1-cyclopropyl-6-fluoro-8-methoxy-7-(3-aminopyrrolidin-1-yl)-3-(2-nitroacetyl)-1,4-dihydro-4-oxoquinoline hydrochloride;

1-cyclopropyl-6-fluoro-8-methyl-7-(3-aminopyrrolidin-1-yl)-3-(2-nitroacetyl)-1,4-dihydro-4-oxoquinoline hydrochloride;

1-cyclopropyl-5-methyl-6-fluoro-7-(3-methylpiperazin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2-amido-2-ethoxycarbonylacetyl)-1,4-dihydro-4-oxoquinoline hydrochloride; and 1-cyclopropyl-6-fluoro-8-chloro-7-(3-aminomethylpyrrolidin-1-yl)-3-(2-nitroacetyl)-1,4-dihydro-4-oxoquinoline hydrochloride.

The quinoline derivatives according to the present invention may be prepared by the processes illustrated hereinbelow.

In these reaction schemes, the abbreviations, Act, $Act_1$, $M^{n+}$, Et, Me and Ac mean a carboxylic acid activating reagent, an carboxyl activating group, and alkali or alkaline earth metal ion, ethyl, methyl and acetyl, respectively, and $R_1$, $R_2$, X, Y and Z are the same as defined in the above formula (I). $R_5$ means $R_3$ having protected amino group, and R means a lower alkyl group such as $CH_3$ or a lower haloalkyl group such as $CF_3$.

The compound of formula (I) according to the present invention may be prepared as follows: A carboxy group of the quinoline compound represented by the following formula (II) is activated with a carboxylic acid activating reagent to give a compound of the following formula (III), the compound (III) thus obtained is then reacted with an alkali or alkaline earth metal salt of a compound having an activated methylene group represented by the formula, Y—$CH_2$—Z to give a compound of the following formula (IV), and finally the deprotection of the compound (IV) is carried out to give the above compound (I). This reaction scheme may be illustrated as follows:

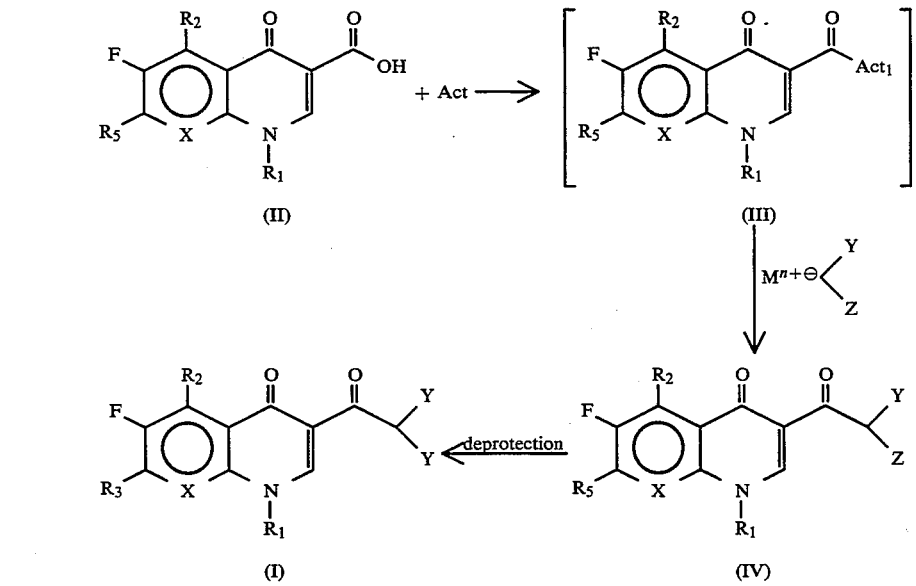

In the above reaction scheme, Act is a carboxy group activating reagent for facilitating the coupling reaction by activating the carboxy group. These activating reagent may be selected from the group consisting of carbonyl diimidazoles, alkoxychloroformates, organic acid anhydrides, carbonates and phosphonates.

$Act_1$ is a carboxyl activating group. The activating group may be —CN, a substituted or unsubstituted phenoxy group, an imidazole group, an activated carbonate group, an activated ester group of organic acid, or a mixed anhydride and the like.

$M^{n+}$ is alkali or alkaline earth metal ions such as $Na^+$, $K^+$ or $Mg^{2+}$.

The deprotection reaction is preferably carried out in a 1–10% HCl-methanol solution, $CF_3CO_2H$ or a 1–10% HCl-ethylacetate solution at a temperature between about 0° and about 80° C.

An alternate process for preparing compounds of formula (I) according to the present invention may be carried out by reversing the role as a nucleophile of a starting material of the above reaction with the reactants (Y—CH$_2$—Z) when the reactivity of these reactants in the substitution reaction is low due to their weak nucleophilicity. That is, in case of Y—CH$_2$—Z compound having an activated methylene group with the weak reactivity, the compound of the following formula (V) is reacted with an acylhalide or an organic acid anhydride to give a compound of the following formula (VI), and then the deprotection reaction of the compound (VI) is carried out to give the following compound (VII) or (VIII). The above reaction may be illustrated hereinbelow.

In the above reaction scheme, compound (V) is prepared from compound (II).

Furthermore, organic acid or inorganic acid salts of compound (I) may be prepared as follows: The salt of the compound (I) synthesized in accordance with the above reaction, for example, its hydrochloride or trifluoroacetate is dissolved in water and the pH of the solution is adjusted to about 7. The resulting solid (base compound) is filtered and then dried. The dried solid is dissolved in a lower alkanol such as methanol or ethanol or a haloalkane such as chloroform dichloromethane or 1,2-dichloroethane or a mixture thereof, and then an equivalent amount of the corresponding acid is added to the mixture to give an acid addition salt of the compound (I). Acids used in the present invention include organic acids such as lactic acid, ascorbic acid, maleic acid, malonic acid, glutamic acid, citric acid, fumaric acid, p-toluenesulfonic acid, acetic acid, trifluoroacetic acid, propionic acid, tartaric acid, succinic acid, methanesulfonic acid and the like; and inorganic acids such as hydrochloric acid, sulfuric acid, nitric acid and the like. All these pharmaceutically acceptable salts are also embraced within the scope of the present invention.

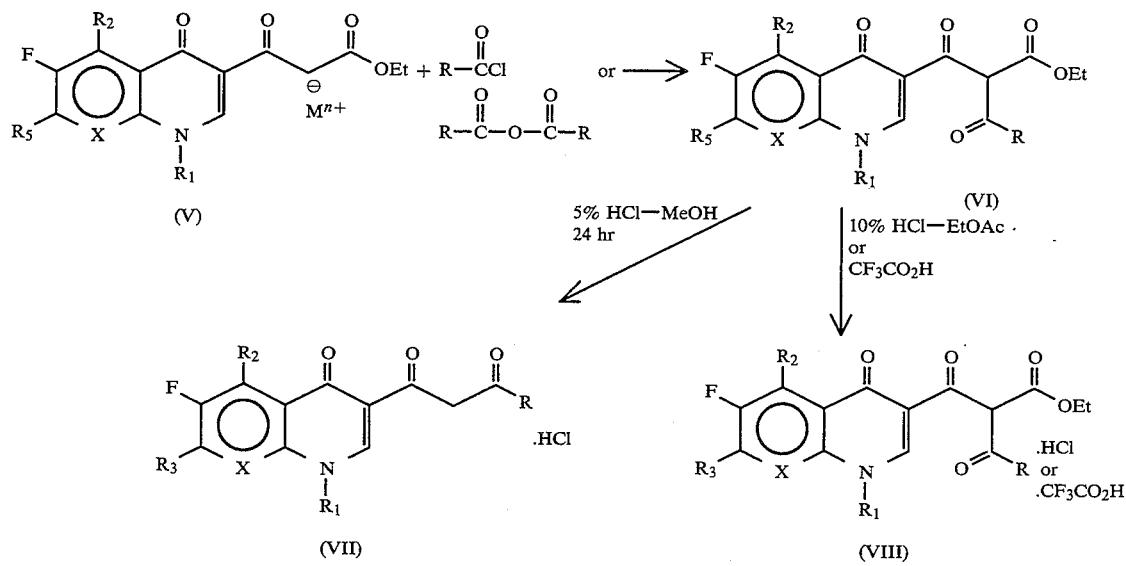

A process for preparing these acid addition salts may be illustrated hereinbelow.

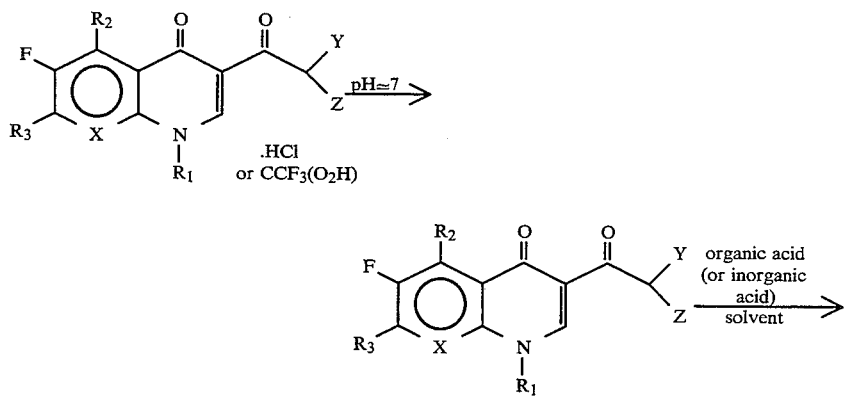

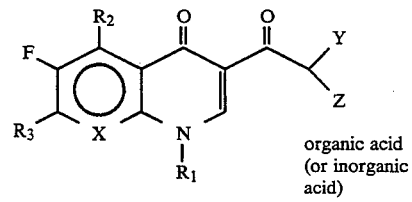

organic acid (or inorganic acid)

Finally, the compounds of the present invention were isolated and purified from the reaction mixture according to conventional method such as a chromatography using ethyl acetate as an eluent.

The compounds according to the present invention are effective particularly against bacteria and bacteroides, and thus useful for the prophylaxis and therapy against a local or systemic infection caused by these pathogens in humans and other animals.

The compounds of the present invention may be administered topically, orally, parenterally or rectally. Among these administrations, a parenteral administration such as an intravenous or intramuscular, or an oral administration is preferred.

In general, it is advantageous to administer the compounds of the present invention in the amount of about 0.1 to about 500 mg/kg, preferably about 0.5 to about 100 mg/kg of body weight per day optionally in divided doses for human or veterinary use. It is advantageous to administer the compounds of the present invention in the amount of about 0.1 to about 200 mg/kg, preferably about 0.3 to about 50 mg/kg of body weight in one single dose. However, it should be understood that the amount of the compound actually administered may be varied beyond the above range of dosages depending on the weight and response of an individual patient, the severity of the patient's symptom, the form of formulation, the chosen route of administration, the number of times or interval of administration and the like. At this time, the optimum dosage and the administration route of the active compound may be determined by those skilled in the art.

One or more compounds of the present invention may be either administered as such, or formulated for administration by mixing therewith non-toxic, inert pharmacodynamically acceptable excipients. The present invention also includes these compounds and pharmaceutical preparations, and processes for preparing them.

Examples of such non-toxic, inert pharmacodynamically acceptable excipients are solid, semi-solid or liquid diluents, fillers and auxiliaries.

Preferred pharmaceutical formulations are tablet, sugar-coated tablet, capsule, granule, suppository, solution, suspension, emulsion, paste, ointment, cream, lotion, powder, spray and the like.

In case of tablet, sugar-coated tablet, capsule and granule, the active compound of the present invention may be combined with conventional excipients, e.g., fillers and extenders such as starch, lactose, sucrose, glucose, mannitol and the like; binders such as carboxymethyl cellulose, alginate, gelatine, polyvinylpyrrolidone and the like; disintegrants such as calcium carbonate, sodium bicarbonate and the like; solution retardants such as paraffin; absorption accelerants such as quarternary ammonium compound and the like; wetting agents such as cetyl alcohol, glycerin monostearate and the like; adsorbents such as kaoline, bentonite and the like; lubricants such as talc, calcium stearate, magnesium stearate, solid polyethylene glycol and the like; or mixtures thereof.

The tablet, sugar-coated tablet; capsule, pill, granule and the like may be coated with conventional coating materials including any opacifier.

The suppository may contain conventional aqueous or nonaqueous excipients, e.g., polyethylene glycol, fat, high molecular ester or mixtures thereof in addition to the active compounds.

The ointment, paste, cream, gel and the like may contain conventional excipients, e.g., animal or vegetable fat, wax, paraffin, starch, cellulose derivatives, polyethylene glycol, bentonite, talc, zinc oxide or mixtures thereof in addition to the active compounds.

The solution or emulsion may contain conventional excipients such as solvent, solubilizer and emulsifier, e.g., water, ethyl alcohol, benzyl benzoate, propylene glycol; oils such as cotton seed oil, peanut oil, corn seed oil or olive oil; fatty acid esters of glycerin, polyethylene glycol or sorbitan, or mixtures thereof in addition to the active compounds.

The solution or emulsion for parenteral administration may contain a sterilized isometric solution or emulsion.

The suspension may contain conventional excipients, e.g., liquid diluents such as water, ethyl alcohol, propylene glycol, or suspending agent.

The above formulations may further contain dyes, preservatives, fragrants, sweeteners and additives.

The formulations may comprise about 0.1 to about 99.5% by weight, preferably about 0.5 to about 95% by weight of the therapeutically active compounds of the present invention.

It will be readily apparent to those skilled in the art that certain changes and modifications may be made to this invention without departing from the spirit or scope of the invention.

The following examples are given to illustrate this invention without limiting them in any way.

EXAMPLE 1

Preparation of 1-cyclopropyl-6-fluoro-7-(4-t-butoxycarbonylpiperazin-1-yl)-1,4-dihydro-4-oxoquinoline-3-carboxylic acid 3.31 g of 1-cyclopropyl-6-fluoro-7-(piperazin-1-yl)-1,4-dihydro-4-oxoquinoline-3-carboxylic acid was dissolved in a mixture of 30 ml of methanol and 20 ml of chloroform, and the resulting solution was stirred at 50° C. for 5 hours after addition of 2.29 g of di-t-butylcarbonate thereto. The solvent was removed under reduced pressure to obtain 4.2 g of the object compound (yield: 97%).

Elementary analysis for $C_{22}H_{26}FN_3O_5$

|  | C (%) | H (%) | N (%) |
| --- | --- | --- | --- |
| Calculated | 61.24 | 6.07 | 9.74 |

| | C (%) | H (%) | N (%) |
|---|---|---|---|
| Found | 62.17 | 6.13 | 9.51 |

EXAMPLE 2

Preparation of 1-cyclopropyl-6-fluoro-7-(4-t-butoxycarbonylpiperazin-1-yl)-1,4-dihydro-4-oxoquinoline-3-carboimidazolide 4.31 g of the compound obtained from Example 1 was dissolved in 50 ml of chloroform, and 1.9 g of carbonylimidazole was added thereto. The resulting mixture was refluxed for 4 hours, and then the solvent was distilled off under reduced pressure to obtain the object compound. This object compound was used without further purification in the following Example.

EXAMPLE 3

Preparation of 1-cyclopropyl-6-fluoro-7-(4-t-butoxycarbonylpiperazin-1-yl)-3-(2-nitroacetyl)-1,4-dihydro-4-oxoquinoline To the compound obtained from Example 2 were added 100 ml of tetrahydrofuran, and then 1.4 g of potassium t-butoxide and 3.05 g of nitromethane in turn. The resulting mixture was refluxed for overnight. The reaction mixture was cooled to room temperature and its pH was adjusted to about 3.3 with 2N HCl. The mixture was extracted three times with 300 ml of ethylacetate, and then purified on a silica gel column chromatography to isolate 4.03 g of the object compound (yield: 85%).

Elementary analysis for $C_{22}H_{27}FN_4O_6$

| | C (%) | H (%) | N (%) |
|---|---|---|---|
| Calculated | 58.22 | 5.74 | 11.81 |
| Found | 58.10 | 5.79 | 11.71 |

EXAMPLE 4

Preparation of 1-cyclopropyl-6-fluoro-7-(piperazin-1-yl)-3-(2-nitroacetyl)-1,4-dihydro-4-oxoquinoline hydrochloride (Process 1)

4.7 g of 1-cyclopropyl-6-fluoro-7-(4-t-butoxycarbonylpiperazin-1-yl)-3-(2-nitroacetyl)-1,4-dihydro-4-oxoquinoline obtained from Example 3 was dissolved in 50 ml of 5% HCl-methanol solution and then stirred at room temperature for 5 hours.

The solvent was distilled off under reduced pressure, and the solid formed after addition of 50 ml of acetone was filtered to obtain 2.96 g of the above object compound (yield: 72%).

Elementary analysis for $C_{18}H_{20}ClFN_4O_4$

| | C (%) | H (%) | N (%) |
|---|---|---|---|
| Calculated | 52.62 | 4.91 | 13.64 |
| Found | 52.55 | 4.99 | 13.53 |

(Process 2)

4.7 g of 1-cyclopropyl-6-fluoro-7-(4-t-butoxycarbonylpiperazin-1-yl)-3-(2-nitroacetyl)-1,4-dihydro-4-oxoquinoline obtained from Example 3 was dissolved in 50 ml of 10% HCl-ethylacetate solution, and the resulting solid was filtered and then dried to obtain 3.78 g of the above object compound (yield: 92%).

Elementary analysis for $C_{18}H_{20}ClFN_4O_4$

| | C (%) | H (%) | N (%) |
|---|---|---|---|
| Calculated | 52.62 | 4.91 | 13.64 |
| Found | 52.55 | 4.99 | 13.53 |

EXAMPLE 5

Preparation of 1-cyclopropyl-6-fluoro-7-(piperazin-1-yl)-3-(2-nitroacetyl)-1,4-dihydro-4-oxoquinoline trifluoroacetate 4.7 g of 1-cyclopropyl-6-fluoro-7-(4-t-butoxycarbonylpiperazin-1-yl)-3-(2-nitroacetyl)-1,4-dihydro-4-oxoquinoline obtained from Example 3 was dissolved in 20 ml of trifluoroacetic acid and then stirred for 10 minutes. The solvent was removed, and the solid formed after addition of 50 ml of acetone was filtered and then dried to obtain 4.25 g of the object compound (yield: 87%).

Elementary analysis for $C_{20}H_{20}F_4N_4C_6$

| | C (%) | H (%) | N (%) |
|---|---|---|---|
| Calculated | 49.19 | 4.13 | 11.47 |
| Found | 49.03 | 4.19 | 11.35 |

EXAMPLE 6

Preparation of 1-cyclopropyl-6,8-difluoro-7-(piperazin-1-yl)-3-(2-nitroacetyl)-1,4-dihydro-4-oxoquinoline hydrochloride 3.5 g of 1-cyclopropyl-6,8-difluoro-7-(piperazin-1-yl)-1,4-dihydro-4-oxoquinoline-3-carboxylic acid as a starting material was subjected to the same processes as described in Examples 1 to 4 to obtain 2.6 g of the object compound (yield: 62%).

Elementary analysis for $C_{18}H_{19}ClF_2N_4O_4$

| | C (%) | H (%) | N (%) |
|---|---|---|---|
| Calculated | 50.42 | 4.47 | 13.07 |
| Found | 50.33 | 4.51 | 12.99 |

EXAMPLE 7

Preparation of 1-cyclopropyl-6,8-difluoro-7-(3-methylpiperazin-1-yl)-3-(2-nitroacetyl)-1,4-dihydro-4-oxoquinoline hydrochloride 3.6 g of 1-cyclopropyl-6,8-difluoro-7-(3-methylpiperazin-1-yl)-1,4-dihydro-4-oxoquinoline-3-carboxylic acid as a starting material was subjected to the same processes as described in Examples 1 to 4 to obtain 1.82 g of the object compound (yield: 41%).

Elementary analysis for $C_{19}H_{21}ClF_2N_4O_4$

|  | C (%) | H (%) | N (%) |
|---|---|---|---|
| Calculated | 51.53 | 4.78 | 12.65 |
| Found | 51.67 | 4.81 | 12.80 |

EXAMPLE 8

Preparation of 1-(2,4-difluorophenyl)-6-fluoro-7-(3-aminopyrrolidin-1-yl)-3-(2-nitroacetyl)-1,4-dihydro-4-oxo-1,8-naphthyridinehydrochloride 4.0 g of 1-(2,4-difluorophenyl)-6-fluoro-7-(3-t-butoxycarbonylaminopyrrolidin-1-yl)-1,4-dihydro-4-oxo-1,8-naphthyridine-3-carboxylic acid as a starting material was subjected to the same processes as described in Examples 2 to 4 to obtain 2.47 g of the object compound (yield: 51%).

Elementary analysis for $C_{20}H_{17}ClF_3N_5O_4$

|  | C (%) | H (%) | N (%) |
|---|---|---|---|
| Calculated | 49.65 | 3.54 | 14.47 |
| Found | 49.58 | 3.59 | 14.39 |

EXAMPLE 9

Preparation of 1-(2,4-difluorophenyl)-6-fluoro-7-(3-aminopyrrolidin-1-yl)-3-(2-nitroacetyl)-1,4-dihydro-4-oxoquinoline hydrochloride 5.0 g of 1-(2,4-difluorophenyl)-6-fluoro-7-(3-butoxycarbonylaminopyrrolidin-1-yl)-1,4-dihydro-4-oxoquinoline-3-carboxylic acid as a starting material was subjected to the same processes as described in Examples 2 to 4 to obtain 2.12 g of the object compound (yield: 44%).

Elementary analysis for $C_{21}H_{18}ClF_3N_4O_4$

|  | C (%) | H (%) | N (%) |
|---|---|---|---|
| Calculated | 52.24 | 3.76 | 11.60 |
| Found | 52.21 | 3.80 | 11.65 |

EXAMPLE 10

Preparation of 1-(2,4-difluorophenyl)-6-fluoro-7-(3-methylpiperazin-1-yl)-3-(2-nitroacetyl)-1,4-dihydro-4-oxoquinoline hydrochloride 4.2 g of 1-(2,4-difluorophenyl)-6-fluoro-7-(3-methylpiperazin-1-yl)-1,4-dihydro-4-oxoquinoline-3-carboxylic acid as a starting material was subjected to the same processes as described in Examples 1 to 4 to obtain 1.54 g of the object compound (yield: 31%).

Elementary analysis for $C_{22}H_{20}ClF_3N_4O_4$

|  | C (%) | H (%) | N (%) |
|---|---|---|---|
| Calculated | 53.18 | 4.06 | 11.28 |
| Found | 53.30 | 4.11 | 11.21 |

EXAMPLE 11

Preparation of 1-cyclopropyl-6-fluoro-8-chloro-7-(3-aminopyrrolidin-1-yl)-3-(2-nitroacetyl)-1,4-dihydro-4-oxoquinoline hydrochloride 4.6 g of 1-cyclopropyl-6-fluoro-8-chloro-7-(3-t-butoxycarbonylaminopyrrolidin-1-yl)-1,4-dihydro-4-oxoquinoline-3-carboxylic acid as a starting material was subjected to the same processes as described in Examples 2 to 4 to obtain 2.18 g of the object compound (yield: 49%).

Elementary analysis for $C_{18}H_{19}Cl_2FN_4O_4$

|  | C (%) | H (%) | N (%) |
|---|---|---|---|
| Calculated | 48.55 | 4.30 | 12.58 |
| Found | 48.49 | 4.40 | 12.51 |

EXAMPLE 12

Preparation of 1-cyclopropyl-6-fluoro-8-chloro-7-(3-3R-aminopyrrolidin-1-yl)-3-(2-nitroacetyl)-1,4-dihydro-4-oxoquinoline hydrochloride 4.6 g of 1-cyclopropyl-6-fluoro-8-chloro-7-(3-3R-t-butoxycarbonylaminopyrrolidin-1 1-yl)-1,4-dihydro-4-oxoquinoline-3-carboxylic acid as a starting material was subjected to the same processes as described in Examples 2 to 4 to obtain 2.0 g of the object compound (yield: 45%).

Elementary analysis for $C_{18}H_{19}Cl_2FN_4O_4$

|  | C (%) | H (%) | N (%) |
|---|---|---|---|
| Calculated | 48.55 | 4.30 | 12.58 |
| Found | 48.41 | 4.38 | 12.55 |

EXAMPLE 13

Preparation of 1-cyclopropyl-6-fluoro-8-chloro-7-(3-3S-aminopyrrolidin-1-yl)-3-(2-nitroacetyl)-1,4-dihydro-4-oxoquinoline hydrochloride 4.6 g of 1-cyclopropyl-6-fluoro-8-chloro-7-(3-3S-t-butoxycarbonylaminopyrrolidin-1-yl)-1,4-dihydro-4-oxoquinoline-3-carboxylic acid as a starting material was subjected to the same processes as described in Examples 2 to 4 to obtain 2.45 g of the object compound (yield: 55%).

Elementary analysis for $C_{18}H_{19}Cl_2FN_4O_4$

|  | C (%) | H (%) | N (%) |
|---|---|---|---|
| Calculated | 48.55 | 4.30 | 12.58 |
| Found | 48.46 | 4.35 | 12.49 |

EXAMPLE 14

Preparation of 1-cyclopropyl-5-amino-6,8-difluoro-7-(3,5-cis-dimethylpiperazin-1-yl)-3-(2-nitroacetyl)-1,4-dihydro-4-oxoquinoline hydrochloride 3.9 g of 1-cyclopropyl-5-amino-6,8-difluoro-7-(3,5-cis-dimethylpiperazin-1-yl-1,4-dihydro-4-oxoquinoline-3-carboxylic acid as a starting material was subjected to the same processes as described in Examples 1 to 4 to obtain 1.18 g of the object compound (yield: 25%).

Elementary analysis for $C_{20}H_{24}ClF_2N_5O_4$

|  | C (%) | H (%) | N (%) |
| --- | --- | --- | --- |
| Calculated | 50.91 | 5.13 | 14.84 |
| Found | 51.01 | 5.15 | 14.90 |

EXAMPLE 15

Preparation of 1-cyclopropyl-6,8-difluoro-7-(3-methylaminomethyl-2,5-dihydropyrrol-1-yl)-3-(2-nitroacetyl)-1,4-dihydro-4-oxoquinoline hydrochloride 3.8 g of 1-cyclopropyl-6,8-difluoro-7-(3-methylaminomethyl-2,5-dihydropyrrol-1-yl)-1,4-dihydro-4-oxoquinoline-3-carboxylic acid as a starting material was subjected to the same processes as described in Examples 1 to 4 to obtain 1.68 g of the object compound (yield: 37%).

Elementary analysis for $C_{20}H_{21}ClF_2N_4O_4$

|  | C (%) | H (%) | N (%) |
| --- | --- | --- | --- |
| Calculated | 52.81 | 4.65 | 12.32 |
| Found | 52.77 | 4.68 | 12.30 |

EXAMPLE 16

Preparation of 1-cyclopropyl-6-fluoro-8-chloro-7-(3-methylaminomethyl-2,5-dihydropyrrol-1-yl)-3-(2-nitroacetyl)-1,4-dihydro-4-oxoquinoline hydrochloride 3.9 g of 1-cyclopropyl-6-fluoro-8-chloro-7-(3-methylaminomethyl-2,5-dihydropyrrol-1-yl)-1,4-dihydro-4-oxoquinoline-3-carboxylic acid as a starting material was subjected to the same processes as described in Examples 1 to 4 to obtain 1.36 g of the object compound (yield: 29%).

Elementary analysis for $C_{20}H_{21}Cl_2FN_4O_4$

|  | C (%) | H (%) | N (%) |
| --- | --- | --- | --- |
| Calculated | 50.97 | 4.49 | 11.89 |
| Found | 51.05 | 4.51 | 11.83 |

EXAMPLE 17

Preparation of 1-cyclopropyl-6-fluoro-7-(4-t-butoxycarbonylpiperazin-1-yl)-3-(2,2-diethoxycarbonylacetyl)-1,4-dihydro-4-oxoquinoline 4.3 g of 1-cyclopropyl-6-fluoro-7-(4-t-butoxycarbonylpiperazin-1-yl)-1,4-dihydro-4-oxoquinoline-3-carboxylic acid obtained from Example 1 was dissolved in 100 ml of dichloromethane, and then 1.03 ml of ethylchloroformate was added thereto. The reaction mixture was cooled to 0° C., and then 1.46 ml of triethylamine was slowly added thereto. Magnesium salt of diethylmalonate formed from 1.17 g of Mg(OEt)$_2$ and 1.6 g of diethylmalonate was dissolved in 30 ml of diethyl ether, and this solution was slowly added dropwise to the above reaction solution. The reaction mixture was stirred at room temperature for 5 hours. The pH of the reaction mixture was adjusted to about 3 with 1N-HCl, and the mixture was extracted three times with 500 ml of ethylacetate.

The reaction mixture was dehydrated with anhydrous magnesium sulfate (MgSO$_4$), and then the solvent was distilled off under vacuum. The residue was purified on a silica gel column chromatography to obtain 3.67 g of the object compound (yield: 64%).

Elementary analysis for $C_{29}H_{36}FN_3O_8$

|  | C (%) | H (%) | N (%) |
| --- | --- | --- | --- |
| Calculated | 60.72 | 6.33 | 7.33 |
| Found | 60.66 | 6.41 | 7.25 |

EXAMPLE 18

Preparation of 1-cyclopropyl-6-fluoro-7-(piperazin-1-yl)-3-(2,2-diethoxycarbonylacetyl)-1,4-dihydro-4-oxoquinoline hydrochloride 5.74 g of the compound obtained from Example 17 was dissolved in 100 ml of 10% HCl-ethylacetate solution, and the solution was stirred for 2 hours. The resulting solid was filtered, and then dried to obtain 4.95 g of the object compound (yield: 97%).

Elementary analysis for $C_{24}H_{29}ClFN_3O_6$

|  | C (%) | H (%) | N (%) |
| --- | --- | --- | --- |
| Calculated | 56.53 | 5.73 | 8.24 |
| Found | 56.55 | 5.74 | 8.21 |

EXAMPLE 19

Preparation of 1-cyclopropyl-6-fluoro-7-(piperazin-1-yl)-3-(2-ethoxycarbonylacetyl)-1,4-dihydro-4-oxoquinoline hydrochloride 5.74 g of the compound obtained from Example 17 was dissolved in 200 ml of 5% HCl-methanol solution, and then 0.5 ml of distilled water was added thereto. This solution was stirred at room temperature for 24 hours. The solvent was distilled off and concentrated under reduced pressure. 20 ml of acetone and 100 ml of diethyl ether were added thereto, and the resulting solid was filtered and then dried to obtain 2.71 g of the object compound (yield: 62%).

Elementary analysis for $C_{21}H_{25}ClFN_3O_4$

|  | C (%) | H (%) | N (%) |
| --- | --- | --- | --- |
| Calculated | 57.60 | 5.75 | 9.60 |
| Found | 57.57 | 5.84 | 9.50 |

EXAMPLE 20

Preparation of 1-cyclopropyl-6,8-difluoro-7-(3-aminopyrrolidin-1-yl)-3-(2,2-diethoxycarbonylacetyl)-1,4-dihydro-4-oxoquinoline hydrochloride 4.5 g of 1-cyclopropyl-6,8-difluoro-7-(3-t-butoxycarbonylaminopyrrolidin-1-yl)-1,4-dihydro-4-oxoquinoline-3-carboxylic acid as a starting material was subjected to the same processes as described in Examples 17 and 18 to obtain 2.69 g of the object compound (yield: 51%).

Elementary analysis for $C_{24}H_{28}ClF_2N_3O_6$

|  | C (%) | H (%) | N (%) |
|---|---|---|---|
| Calculated | 54.60 | 5.35 | 7.96 |
| Found | 54.59 | 5.36 | 7.95 |

EXAMPLE 21

Preparation of 1-cyclopropyl-6,8-difluoro-7-(3-aminopyrrolidin-1-yl)-3-(2-ethoxycarbonylacetyl)-1,4-dihydro-4-oxoquinoline hydrochloride 4.5 g of 1-cyclopropyl-6,8-difluoro-7-(3-t-butoxycarbonylaminopyrrolidin-1-yl)-1,4-dihydro-4-oxoquinoline-3-carboxylic acid as a starting material was subjected to the same processes as described in Examples 17 and 19 to obtain 1.46 g of the object compound (yield: 32%).

Elementary analysis for $C_{21}H_{24}ClF_2N_3O_4$

|  | C (%) | H (%) | N (%) |
|---|---|---|---|
| Calculated | 55.33 | 5.31 | 9.22 |
| Found | 55.21 | 5.39 | 9.18 |

EXAMPLE 22

Preparation of 1-cyclopropyl-6-fluoro-8-chloro-7-(3-aminopyrrolidin-1-yl)-3-(2,2-diethoxycarbonylacetyl)-1,4-dihydro-4-oxoquinoline hydrochloride 4.7 g of 1-cyclopropyl-6-fluoro-8-chloro-7-(3-t-butoxycarbonylaminopyrrolidin-1-yl)-1,4-dihydro-4-oxoquinoline-3-carboxylic acid as a starting material was subjected to the same process as described in Example 20 to obtain 3.1 g of the object compound (yield: 57%).

Elementary analysis for $C_{24}H_{28}Cl_2FN_3O_6$

|  | C (%) | H (%) | N (%) |
|---|---|---|---|
| Calculated | 52.95 | 5.18 | 7.72 |
| Found | 52.99 | 5.20 | 7.71 |

EXAMPLE 23

Preparation of 1-cyclopropyl-6-fluoro-8-chloro-7-(3-3R-aminopyrrolidin-1-yl)-3-(2,2-diethoxycarbonylacetyl)-1,4-dihydro-4-oxoquinoline hydrochloride 4.7 g of 1-cyclopropyl-6-fluoro-8-chloro-7-(3-3R-t-butoxycarbonylaminopyrrolidin-1-yl)-1,4-dihydro-4-oxoquinoline-3-carboxylic acid as a starting material was subjected to the same process as described in Example 20 to obtain 3.32 g of the object compound (yield: 61%).

Elementary analysis for $C_{24}H_{28}Cl_2FN_3O_6$

|  | C (%) | H (%) | N (%) |
|---|---|---|---|
| Calculated | 52.95 | 5.18 | 7.72 |
| Found | 52.83 | 5.22 | 7.70 |

EXAMPLE 24

Preparation of 1-cyclopropyl-6-fluoro-8-chloro-7-(3-3S-aminopyrrolidin-1-yl)-3-(2,2-diethoxycarbonylacetyl)-1,4-dihydro-4-oxoquinoline hydrochloride 4.7 g of 1-cyclopropyl-6-fluoro-8-chloro-7-(3-3S-t-butoxycarbonylaminopyrrolidin-1-yl)-1,4-dihydro-4-oxoquinoline-3-carboxylic acid as a starting material was subjected to the same process as described in Example 20 to obtain 2.99 g of the object compound (yield: 55%).

Elementary analysis for $C_{24}H_{28}Cl_2FN_3O_6$

|  | C (%) | H (%) | N (%) |
|---|---|---|---|
| Calculated | 52.95 | 5.18 | 7.72 |
| Found | 53.00 | 5.20 | 7.71 |

EXAMPLE 25

Preparation of 1-cyclopropyl-6-fluoro-8-chloro-7-(3-aminopyrrolidin-1-yl)-3-(2-ethoxycarbonylacetyl)-1,4-dihydro-4-oxoquinoline hydrochloride 4.7 g of 1-cyclopropyl-6-fluoro-8-chloro-7-(3-t-butoxycarbonylaminopyrrolidin-1-yl)-1,4-dihydro-4-oxoquinoline-3-carboxylic acid as a starting material was subjected to the same process as described in Example 21 to obtain 1.08 g of the object compound (yield: 23%).

Elementary analysis for $C_{21}H_{24}Cl_2FN_3O_4$

|  | C (%) | H (%) | N (%) |
|---|---|---|---|
| Calculated | 53.40 | 5.12 | 8.90 |
| Found | 53.34 | 5.17 | 8.88 |

EXAMPLE 26

Preparation of 1-cyclopropyl-6-fluoro-8-chloro-7-(3-3R-aminopyrrolidin-1-yl)-3-(2-ethoxycarbonylacetyl)-1,4-dihydro-4-oxoquinoline hydrochloride 4.7 g of 1-cyclopropyl-6-fluoro-8-chloro-7-(3-3R-t-butoxycarbonylaminopyrrolidin-1-yl)-1,4-dihydro-4-oxoquinoline-3-carboxylic acid as a starting material was subjected to the same process as described in Example 21 to obtain 1.42 g of the object compound (yield: 30%).

Elementary analysis for $C_{21}H_{24}Cl_2FN_3O_4$

|  | C (%) | H (%) | N (%) |
|---|---|---|---|
| Calculated | 53.40 | 5.12 | 8.90 |
| Found | 53.48 | 5.15 | 8.89 |

EXAMPLE 27

Preparation of
1-cyclopropyl-6-fluoro-8-chloro-7-(3-3S-aminopyrrolidin-1-yl)-3-(2-ethoxycarbonylacetyl)-1,4-dihydro-4-oxoquinoline hydrochloride 4.7 g of 1-cyclopropyl-6-fluoro-8-chloro-7-(3-3S-t-butoxycarbonylaminopyrrolidin-1-yl)-1,4-dihydro-4-oxoquinoline-3-carboxylic acid as a starting material was subjected to the same process as described in Example 21 to obtain 1.32 g of the object compound
(yield: 28%).

Elementary analysis for $C_{21}H_{24}Cl_2FN_3O_4$

|  | C (%) | H (%) | N (%) |
| --- | --- | --- | --- |
| Calculated | 53.40 | 5.12 | 8.90 |
| Found | 53.31 | 5.17 | 8.88 |

EXAMPLE 28

Preparation of
1-cyclopropyl-6-fluoro-8-chloro-7-(3-methylaminomethyl-2,5-dihydropyrrol-1-yl)-3-(2,2-diethoxycarbonylacetyl)-1,4-dihydro-4-oxoquinoline hydrochloride 4.9 g of 1-cyclopropyl-6-fluoro-8-chloro-7-(3-(N-methyl-t-butoxycarbonylamino)-methyl-2,5-dihydropyrrol-1-yl)-1,4-dihydro-4-oxoquinoline-3-carboxylic acid as a starting material was subjected to the same process as described in Example 20 to obtain 3.59 g of the object compound
(yield: 63%).

Elementary analysis for $C_{26}H_{30}Cl_2FN_3O_6$

|  | C (%) | H (%) | N (%) |
| --- | --- | --- | --- |
| Calculated | 54.74 | 5.30 | 7.37 |
| Found | 54.77 | 5.31 | 7.38 |

EXAMPLE 29

Preparation of
1-cyclopropyl-6-fluoro-8-chloro-7-(3-methylaminomethyl-2,5-dihydropyrrol-1-yl)-3-(2-ethoxycarbonylacetyl)-1,4-dihydro-4-oxoquinoline hydrochloride 4.9 g of 1-cyclopropyl-6-fluoro-8-chloro-7-(3-(N-methyl-t-butoxycarbonylamino)-methyl-2,5-dihydropyrrol-1-yl)-1,4-dihydro-4-oxoquinoline-3-carboxylic acid as a starting material was subjected to the same process as described in Example 21 to obtain 1.34 g of the object compound
(yield: 27%).

Elementary analysis for $C_{23}H_{26}Cl_2FN_3O_4$

|  | C (%) | H (%) | N (%) |
| --- | --- | --- | --- |
| Calculated | 55.43 | 5.26 | 8.43 |
| Found | 55.35 | 5.30 | 8.40 |

EXAMPLE 30

Preparation of
1-ethyl-6,8-difluoro-7-(3-aminopyrrolidin-1-yl)-3-(2-nitroacetyl)-1,4-dihydro-4-oxoquinoline hydrochloride 4.4 g of 1-ethyl-6,8-difluoro-7-(3-t-butoxycarbonylaminopyrrolidin-1-yl)-1,4-dihydro-4-oxoquinoline-3-carboxylic acid as a starting material was subjected to the same process as described in Example 9 to obtain 2.25 g of the object compound
(yield: 54%).

Elementary analysis for $C_{17}H_{19}ClF_2N_4O_4$

|  | C (%) | H (%) | N (%) |
| --- | --- | --- | --- |
| Calculated | 48.99 | 4.59 | 13.44 |
| Found | 49.02 | 4.61 | 13.38 |

EXAMPLE 31

Preparation of
1-(2-fluoroethyl)-6,8-difluoro-7-(3-aminopyrrolidin-1-yl)-3-(2-nitroacetyl)-1,4-dihydro-4-oxoquinoline hydrochloride 4.6 g of 1-(2-fluoroethyl)-6,8-difluoro-7-(3-t-butoxycarbonylaminopyrrolidin-1-yl)-1,4-dihydro-4-oxoquinoline-3-carboxylic acid as a starting material was subjected to the same process as described in Example 9 to obtain 1.96 g of the object compound
(yield: 45%).

Elementary analysis for $C_{17}H_{18}ClF_3N_4O_4$

|  | C (%) | H (%) | N (%) |
| --- | --- | --- | --- |
| Calculated | 46.96 | 4.17 | 12.89 |
| Found | 47.01 | 4.18 | 12.87 |

EXAMPLE 32

Preparation of
1-cyclopropyl-6-fluoro-8-chloro-7-(3-t-butoxycarbonylaminopyrrolidin-1-yl)-3-(2-methanesulfonylacetyl)-1,4-dihydro-4-oxoquinoline hydrochloride 4.7 g of 1-cyclopropyl-6-fluoro-8-chloro-7-(3-t-butoxycarbonylaminopyrrolidin-1-yl)-1,4-dihydro-4-oxoquinoline-3-carboxylic acid was dissolved in 20 ml of ethyleneglycol dimethylether, and 1.94 g of carbonyl diimidazole was added thereto. The resulting reaction mixture was refluxed for 4 hours. 1.97 g of dimethylsulfone and 0.84 g of 60% sodium hydride were stirred in 20 ml of a mixture (1:2) of dimethylsulfoxide and ethyleneglycol dimethylether at 60° C. for 1 hour to obtain sodium dimethylsulfonate. Sodium dimethylsulfonate thus obtained was added to the above reaction mixture, and then reacted at 60° C. for 2 hours. The reaction mixture was acidified with 2 ml of anhydrous acetic acid, extracted three times with 300 ml of ethylacetate, and then dehydrated with MgSO4. The solvent was distilled off under reduced pressure. The residue was purified on a silica gel column chromatography to obtain 3.58 g of the object compound
(yield: 66%).

Elementary analysis for $C_{24}H_{29}ClFN_3O_6S$

|  | C (%) | H (%) | N (%) |
| --- | --- | --- | --- |
| Calculated | 53.18 | 5.39 | 7.75 |
| Found | 53.09 | 5.44 | 7.71 |

EXAMPLE 33

Preparation of 1-cyclopropyl-6-fluoro-8-chloro-7-(3-aminopyrrolidin-1-yl)-3-(2-methanesulfonylacetyl)-1,4-dihydro-4-oxoquinoline hydrochloride 5.4 g of the compound obtained from Example 32 was dissolved in 10% HCl-ethylacetate solution, and then stirred for 30 minutes. The resulting solid was filtered, and then dried to obtain 4.49 g of the object compound (yield: 94%).

Elementary analysis for $C_{19}H_{22}Cl_2FN_3O_4S$

|  | C (%) | H (%) | N (%) |
| --- | --- | --- | --- |
| Calculated | 47.71 | 4.64 | 8.78 |
| Found | 47.73 | 4.64 | 8.77 |

EXAMPLE 34

Preparation of 1-cyclopropyl-6-fluoro-8-chloro-7-(3,7-diazabicyclo[3.3.0]oct-1,5-en-3-yl)-3-(2-nitroacetyl)-1,4-dihydro-4-oxoquinoline hydrochloride 3.9 g of 1-cyclopropyl-6-fluoro-8-chloro-7-(3,7-diazabicyclo[3.3.0]oct-1,5-en-3-yl)-1,4-dihydro-4-oxoquinoline-3-carboxylic acid as a starting material was subjected to the same processes as described in Examples 1 to 4 to obtain 2.2 g of the object compound (yield: 47%).

Elementary analysis for $C_{20}H_{19}Cl_2FN_4O_4$

|  | C (%) | H (%) | N (%) |
| --- | --- | --- | --- |
| Calculated | 51.19 | 4.08 | 11.94 |
| Found | 51.27 | 4.11 | 11.91 |

EXAMPLE 35

Preparation of 1-cyclopropyl-6-fluoro-8-chloro-7-(7-amino-5-azaspiro[2.4]hept-5-yl)-3-(2-nitroacetyl)-1,4-dihydro-4-oxoquinoline hydrochloride 4.9 g of 1-cyclopropyl-6-fluoro-8-chloro-7-(7-t-butoxycarbonylamino-5-azaspiro[2.4]hept-5-yl)-1,4-dihydro-4-oxoquinoline-3-carboxylic acid as a starting material was subjected to the same processes as described in Examples 2 to 4 to obtain 1.93 g of the object compound (yield: 41%).

Elementary analysis for $C_{20}H_{21}Cl_2FN_4O_4$

|  | C (%) | H (%) | N (%) |
| --- | --- | --- | --- |
| Calculated | 50.97 | 4.49 | 11.89 |
| Found | 50.95 | 4.52 | 11.85 |

EXAMPLE 36

Preparation of 1-cyclopropyl-6-fluoro-8-chloro-7-(3,7-diazabicyclo[3.3.0]oct-1,5-en-3-yl)-3-(2,2-diethoxycarbonylacetyl)-1,4-dihydro-4-oxoquinoline hydrochloride 3.9 g of 1-cyclopropyl-6-fluoro-8-chloro-7-(3,7-diazabicyclo[3.3.0]oct-1,5-en-3-yl)-1,4-dihydro-4-oxoquinoline-3-carboxylic acid as a starting material was subjected to the same processes as described in Examples 1, 17 and 18 to obtain 1.42 g of the object compound (yield: 25%).

Elementary analysis for $C_{26}H_{28}Cl_2FN_3O_6$

|  | C (%) | H (%) | N (%) |
| --- | --- | --- | --- |
| Calculated | 54.94 | 4.97 | 7.39 |
| Found | 54.98 | 4.99 | 7.38 |

EXAMPLE 37

Preparation of 1-cyclopropyl-6-fluoro-8-chloro-7-(3-aminopyrrolidin-1-yl)-3-(2-acetoacetyl)-1,4-dihydro-4-oxoquinoline hydrochloride 4.7 g of 1-cyclopropyl-6-fluoro-8-chloro-7-(3-aminopyrrolidin-1-yl)-3-(2-ethoxycarbonylacetyl)-1,4-dihydro-4-oxoquinoline hydrochloride obtained from Example 25 was dissolved in 100 ml of MeOH, and then 3 ml of Et$_3$N was added thereto. 2.18 g of di-t-butyldicarbonate was added to the above reaction mixture, and then stirred at 50° C. for 2 hours. The solvent was distilled off under reduced pressure. Water and ethylacetate were added to the residue. The pH of the reaction mixture was adjusted to about 5 with 1N HCl, and then the organic layer was separated. The organic layer thus separated was dehydrated with anhydrous MgSO$_4$, and then the solvent was removed to obtain 5.09 g of 1-cyclopropyl-6-fluoro-8-chloro-7-(3-t-butoxycarbonylpyrrolidin-1-yl)-3-(2-ethoxycarbonylacetyl)-1,4-dihydro-4-oxoquinoline (yield: 95%).

The compound thus obtained was dissolved in 50 ml of toluene, and 1.2 g of Mg(OEt)$_2$ was added thereto. The reaction mixture was acetylated with 0.74 ml of acetyl chloride. The reaction mixture was stirred at room temperature for 3 hours, and 100 ml of water was added thereto. The pH of the reaction mixture was adjusted to about 3 with 1N HCl, and then extracted three times with 300 ml of ethyl acetate. The organic layer was separated, and then dehydrated with anhydrous MgSO$_4$. The solvent was distilled off under reduced pressure, and then the residue was separated on silica gel. The solvent was removed, and 100 ml of 5% HCl-MeOH solution was added thereto. The reaction mixture was stirred at 25° C. for 24 hours, and then the solvent was distilled off under reduced pressure at low temperature. A little amount of mixture (3:1) of ethyl ether and acetone was added to the above concentrated reaction mixture, and the resulting solid was filtered, and then dried to obtain 1.17 g of the object compound (yield: 28%).

Elementary analysis for $C_{20}H_{22}Cl_2FN_3O_3$

|  | C (%) | H (%) | N (%) |
|---|---|---|---|
| Calculated | 54.31 | 5.01 | 9.50 |
| Found | 54.26 | 5.10 | 9.47 |

EXAMPLE 38

Preparation of 1-cyclopropyl-6-fluoro-8-chloro-7-(3-aminopyrrolidin-1-yl)-3-(2-trifluoroacetoacetyl)-1,4-dihydro-4-oxoquinoline hydrochloride 4.7 g of 1-cyclopropyl-6-fluoro-8-chloro-7-(3-aminopyrrolidin-1-yl)-3-(2-ethoxycarbonylacetyl)-1,4-dihydro-4-oxoquinoline hydrochloride obtained from Example 25 and 2.1 g of trifluoroacetic acid anhydride as starting materials were subjected to the same process as described in Example 37 to obtain 0.89 g of the object compound (yield: 18%).

Elementary analysis for $C_{20}H_{19}Cl_2F_4N_3O_3$

|  | C (%) | H (%) | N (%) |
|---|---|---|---|
| Calculated | 48.40 | 3.86 | 8.47 |
| Found | 48.46 | 3.88 | 8.45 |

EXAMPLE 39

Preparation of 1-cyclopropyl-6-fluoro-8-chloro-7-(3-aminopyrrolidin-1-yl)-3-(2-cyano-2-ethoxycarbonylacetyl)-1,4-dihydro-4-oxoquinoline hydrochloride 5.2 g of 1-cyclopropyl-6-fluoro-8-chloro-7-(3-t-butoxycarbonylaminopyrrolidin-1-yl)-1,4-dihydro-4-oxoquinoline-3-carboxylic acid imidazolide and 6.9 g of potassium carbonate were put into 200 ml of acetonitrile, and 5.66 g of ethyl cyanoacetate was added thereto, and then refluxed under heating for 5 hours. Acetonitrile was distilled off under reduced pressure, and then water and ethyl acetate were added thereto. The pH of the reaction mixture was adjusted to about 3 with 1N-HCl, and then the organic layer was separated. The organic layer was dehydrated with anhydrous MgSO4, and the solvent was distilled off under reduced pressure. The residue was purified on a silica gel column chromatography, and 50 ml of 10% HCl-ethyl acetate was added to the purified compound. The reaction mixture was stirred for 30 minutes, and the resulting solid was filtered, and then dried to obtain 3.4 g of the object compound (yield: 69%).

Elementary analysis for $C_{22}H_{23}Cl_2FN_4O_4$

|  | C (%) | H (%) | N (%) |
|---|---|---|---|
| Calculated | 53.13 | 4.66 | 11.26 |
| Found | 52.98 | 4.71 | 11.40 |

EXAMPLE 40

Preparation of 1-cyclopropyl-6-fluoro-8-chloro-7-(3-methylaminomethyl-2,5-dihydropyrrol-1-yl)-3-(2-cyano-2-ethoxycarbonylacetyl)-1,4-dihydro-4-oxoquinoline hydrochloride 5.8 g of 1-cyclopropyl-6-fluoro-8-chloro-7-(3-(N-methyl-t-butoxycarbonylamino)methyl-2,5-dihydropyrrol-1-yl)-1,4-dihydro-4-oxoquinoline-3-carboxylic acid imidazolide and 5.66 g of ethyl cyanoacetate as starting materials were subjected to the same process as described in Example 39 to obtain 2.80 g of the object compound (yield: 55%).

Elementary analysis for $C_{24}H_{25}Cl_2FN_4O_4$

|  | C (%) | H (%) | N (%) |
|---|---|---|---|
| Calculated | 55.08 | 4.81 | 10.70 |
| Found | 55.21 | 4.85 | 10.66 |

EXAMPLE 41

Preparation of 1-cyclopropyl-6-fluoro-8-chloro-7-(3,7-diazabicyclo[3.3.0]oct-1,5-en-3-yl)-3-(2-cyano-2-ethoxycarbonylacetyl)-1,4-dihydro-4-oxoquinoline hydrochloride 5.4 g of 1-cyclopropyl-6-fluoro-8-chloro-7-(7-t-butoxycarbonyl-3,7-diazabicyclo[3.3.0]oct-1,5-en-3-yl)-1,4-dihydro-4-oxoquinoline-3-carboxylic acid imidazolide and 5.66 ml of ethyl cyanoacetate as starting materials were subjected to the same process as described in Example 39 to obtain 1.62 g of the object compound (yield: 31%).

Elementary analysis for $C_{24}H_{23}Cl_2FN_4O_4$

|  | C (%) | H (%) | N (%) |
|---|---|---|---|
| Calculated | 55.29 | 4.45 | 10.75 |
| Found | 55.31 | 4.43 | 10.79 |

EXAMPLE 42

Preparation of 1-cyclopropyl-6-fluoro-8-chloro-7-(3-aminopyrrolidin-1-yl)-3-(2-cyanoacetyl)-1,4-dihydro-4-oxoquinoline hydrochloride The compound obtained from the deprotection step of Example 39 was stirred together with 20 ml of 5% HCl-MeOH solution at 25° C. for 24 hours, and then diethyl ether was added thereto. The resulting solid was filtered, and then dried to obtain 0.47 g of the object compound (yield: 11%).

Elementary analysis for $C_{19}H_{19}Cl_2FN_4O_2$

|  | C (%) | H (%) | N (%) |
|---|---|---|---|
| Calculated | 53.66 | 4.50 | 13.17 |
| Found | 53.72 | 4.52 | 13.21 |

EXAMPLE 43

Preparation of
1-cyclopropyl-6-fluoro-8-chloro-7-(3-methylaminomethyl-2,5-dihydropyrrol-1-yl)-3-(2-cyanoacetyl)-1,4-dihydro-4-oxoquinoline hydrochloride The intermediate obtained from Example 40 was subjected to the same process as described in Example 42 to obtain 0.9 g of the object compound
(yield: 20%).
Elementary analysis for $C_{21}H_{21}Cl_2FN_4O_2$

|  | C (%) | H (%) | N (%) |
|---|---|---|---|
| Calculated | 55.89 | 4.69 | 12.41 |
| Found | 55.99 | 4.73 | 12.42 |

EXAMPLE 44

Preparation of
1-cyclopropyl-6-fluoro-8-chloro-7-(3,7-diazabicyclo[3.3.0]oct-1,5-en-3-yl)-3-(2-cyanoacetyl)-1,4-dihydro-4-oxoquinoline hydrochloride The compound obtained prior to deprotection in Example 41 was subjected to the same process as described in Example 42 to obtain 0.67 of the object compound
(yield: 15%).
Elementary analysis for $C_{21}H_{19}Cl_2FN_4O$

|  | C (%) | H (%) | N (%) |
|---|---|---|---|
| Calculated | 56.14 | 4.26 | 12.47 |
| Found | 56.30 | 4.30 | 12.49 |

EXAMPLE 45

Preparation of
1-cyclopropyl-6-fluoro-8-chloro-7-(3-aminopyrrolidin-1-yl)-3-(2,2-dicyanoacetyl)-1,4-dihydro-4-oxoquinoline hydrochloride 5.2 g of 1-cyclopropyl-6-fluoro-8-chloro-7-(3-t-butoxycarbonylaminopyrrolidin-1-yl)-1,4-dihydro-4-oxoquinoline-3-carboxylic acid imidazolide and 3.30 g of malononitrile as starting materials were subjected to the same process as described in Example 39 to obtain 2.56 g of the object compound
(yield: 57%).
Elementary analysis for $C_{20}H_{18}Cl_2FN_5O_2$

|  | C (%) | H (%) | N (%) |
|---|---|---|---|
| Calculated | 53.35 | 4.03 | 15.55 |
| Found | 53.50 | 4.11 | 15.61 |

EXAMPLE 46

Preparation of
1-cyclopropyl-6-fluoro-8-chloro-7-(3-methylaminomethyl-2,5-dihydropyrrol-1-yl)-3-(2-methanesulfonylacetyl)-1,4-dihydro-4-oxoquinoline hydrochloride 3.9 g of 1-cyclopropyl-6-fluoro-8-chloro-7-(3-methylaminomethyl-2,5-dihydropyrrol-1-yl)-1,4-dihydro-4-oxoquinoline-3-carboxylic acid dissolved in a mixture of 20 ml of methanol and 10 ml of chloroform. 2.29 g of di-t-butyldicarbonate was added to this solution, and the reaction mixture was stirred at 50° C. for 3 hours. The solvent was distilled off under reduced pressure, and then subjected to the same processes as described in Examples 32 and 33 to obtain 3.12 g of the object compound
(yield: 62%).
Elementary analysis for $C_{21}H_{24}Cl_2FN_3O_4S$

|  | C (%) | H (%) | N (%) |
|---|---|---|---|
| Calculated | 50.01 | 4.80 | 8.33 |
| Found | 50.12 | 4.85 | 8.31 |

EXAMPLE 47

Preparation of
1-cyclopropyl-6-fluoro-8-chloro-7-(3,7-diazabicyclo[3.3.0]oct-1,5-en-3-yl)-3-(2-methanesulfonylacetyl)-1,4-dihydro-4-oxoquinoline hydrochloride 3.9 g of 1-cyclopropyl-6-fluoro-8-chloro-7-(3,7-diazabicyclo[3.3.0]oct-1,5-en-3-yl)-1,4-dihydro-4-oxoquinoline-3-carboxylic acid as a starting material was subjected to the same process as described in Example 46 to obtain 2.61 g of the object compound
(yield: 52%).
Elementary analysis for $C_{21}H_{22}Cl_2FN_3O_4S$

|  | C (%) | H (%) | N (%) |
|---|---|---|---|
| Calculated | 50.21 | 4.41 | 8.36 |
| Found | 50.35 | 4.48 | 8.32 |

EXAMPLE 48

Preparation of
1-cyclopropyl-6-fluoro-8-chloro-7-(3-aminopyrrolidin-1-yl)-3-(2,2-diacetoacetyl)-1,4-dihydro-4-oxoquinoline hydrochloride 4.6 g of 1-cyclopropyl-6-fluoro-8-chloro-7-(3-t-butoxycarbonylaminopyrrolidin-1-yl)-1,4-dihydro-4-oxoquinoline-3-carboxylic acid and 1.08 ml of 2,4-pentadione as starting materials were subjected to the same process as described in Example 20 to obtain 2.27 g of the object compound
(yield: 47%).
Elementary analysis for $C_{22}H_{24}Cl_2FN_3O_4$

|  | C (%) | H (%) | N (%) |
|---|---|---|---|
| Calculated | 54.56 | 4.99 | 8.68 |
| Found | 54.66 | 5.04 | 8.61 |

EXAMPLE 49

Preparation of
1-cyclopropyl-6-fluoro-8-methoxy-7-(3-aminopyrrolidin-1-yl)-3-(2-nitroacetyl)-1,4-dihydro-4-oxoquinoline hydrochloride 4.6 g of 1-cyclopropyl-6-fluoro-8-methoxy-7-(3-t-butoxycarbonylaminopyrrolidin-1-yl)-1,4-dihydro-4-oxoquinoline-3-carboxylic acid as a starting material was subjected to the same process as described in Example 9 to obtain 1.94 g of the object compound
(yield: 44%).
Elementary analysis for $C_{19}H_{22}ClFN_4O_5$

|  | C (%) | H (%) | N (%) |
|---|---|---|---|
| Calculated | 51.76 | 5.03 | 12.71 |
| Found | 51.88 | 5.11 | 12.80 |

EXAMPLE 50

Preparation of 1-cyclopropyl-6-fluoro-8-methyl-7-(3-aminopyrrolidin-1-yl)-3-(2-nitroacetyl)-1,4-dihydro-4-oxoquinoline hydrochloride 4.4 g of 1-cyclopropyl-6-fluoro-8-methyl-7-(3-t-butoxycarbonylaminopyrrolidin-1-yl)-1,4-dihydro-4-oxoquinoline-3-carboxylic acid as a starting material was subjected to the same processes as described in Examples 2 to 4 to obtain 1.74 g of the object compound (yield: 41%).

Elementary analysis for $C_{19}H_{22}ClFN_4O_4$

|  | C (%) | H (%) | N (%) |
|---|---|---|---|
| Calculated | 53.71 | 5.22 | 13.19 |
| Found | 53.88 | 5.30 | 13.15 |

EXAMPLE 51

Preparation of 1-cyclopropyl-5-methyl-6-fluoro-7-(3-methylpiperazin-1-yl)-3-(2-nitroacetyl)-1,4-dihydro-4-oxoquinoline hydrochloride 3.6 g of 1-cyclopropyl-5-methyl-6-fluoro-7-(3-methylpiperazin-1-yl)-1,4-dihydro-4-oxoquinoline-3-carboxylic acid as a starting material was subjected to the same processes as described in Examples 1 to 4 to obtain 1.45 g of the object compound (yield: 33%).

Elementary analysis for $C_{20}H_{24}ClFN_4O_4$

|  | C (%) | H (%) | N (%) |
|---|---|---|---|
| Calculated | 54.73 | 5.51 | 12.77 |
| Found | 54.60 | 5.61 | 12.68 |

EXAMPLE 52

Preparation of 1-cyclopropyl-6-fluoro-8-chloro-7-(3-aminopyrrolidin-1-yl)-3-(2-amido-2-ethoxycarbonylacetyl)-1,4-dihydro-4-oxoquinoline hydrochloride 5.2 g of 1-cyclopropyl-6-fluoro-8-chloro-7-(3-t-butoxycarbonylaminopyrrolidin-1-yl)-1,4-dihydro-4-oxoquinoline-3-carboxylic acid imidazolide and 6.55 g of malonamide monoethylester as starting materials were subjected to the same process as described in Example 39 to obtain 1.24 g of the object compound (yield: 24%).

Elementary analysis for $C_{22}H_{25}Cl_2FN_4O_5$

|  | C (%) | H (%) | N (%) |
|---|---|---|---|
| Calculated | 51.27 | 4.89 | 10.87 |
| Found | 51.24 | 4.98 | 10.79 |

EXAMPLE 53

Preparation of 1-cyclopropyl-6-fluoro-8-chloro-7-(3-aminomethylpyrrolidin-1-yl)-3-(2-nitroacetyl)-1,4-dihydro-4-oxoquinoline hydrochloride 4.8 g of 1-cyclopropyl-6-fluoro-8-chloro-7-(3-t-butoxycarbonylaminomethylpyrrolidin-1-yl)-1,4-dihydro-4-oxoquinoline-3-carboxylic acid as a starting material was subjected to the same processes as described in Examples 2 to 4 to obtain 2.39 g of the object compound (yield: 52%).

Elementary analysis for $C_{19}H_{21}Cl_2FN_4O_4$

|  | C (%) | H (%) | N (%) |
|---|---|---|---|
| Calculated | 49.69 | 4.61 | 12.20 |
| Found | 49.53 | 4.69 | 12.13 |

EXAMPLE 54

Preparation of 1-cyclopropyl-6-fluoro-8-chloro-7-(3-N-methyl-3R-t-butoxycarbonylaminopyrrolidin-1-yl)-1,4-dihydro-4-oxoquinoline-3-carboxylic acid 14.67 g of 1-cyclopropyl-6-fluoro-8-chloro-7-(3-3R-methylaminopyrrolidin-1-yl)-1,4-dihydro-4-oxoquinoline-3-carboxylic acid was suspended in 300 ml of methanol, and 8.07 g of di-t-butyldicarbonate was added thereto. The resulting mixture was reacted at room temperature for 6 hours, the solvent was distilled off under reduced pressure, and the solid formed after addition of mixed solvent of some methanol with diethyl ether is filtered, and then dried under reduced pressure to obtain 14.31 g of the object compound (yield: 77%).

Elementary analysis for $C_{23}H_{27}ClFN_3O_5$

|  | C (%) | H (%) | O (%) | N (%) |
|---|---|---|---|---|
| Calculated | 57.56 | 5.67 | 16.67 | 8.76 |
| Found | 57.44 | 5.70 | 16.77 | 8.69 |

EXAMPLE 55

Preparation of 1-cyclopropyl-6-fluoro-8-chloro-7-(3-3R-methylaminopyrrolidin-1-yl)-3-(2,2-diethoxycarbonylacetyl)-1,4-dihydro-4-oxoquinoline hydrochloride 9.6 g of 1-cyclopropyl-6-fluoro-8-chloro-7-(3-N-methyl-3R-t-butoxycarbonylaminopyrrolidin-1-yl)-1,4-dihydro-4-oxoquinoline-3-carboxylic acid as a starting material was subjected to the same process as described in Example 20 to obtain 6.37 g of the object compound (yield: 57%).

Elementary analysis for $C_{25}H_{30}Cl_2FN_3O_6$

|  | C (%) | H (%) | O (%) | N (%) |
|---|---|---|---|---|
| Calculated | 53.77 | 5.41 | 17.19 | 7.52 |
| Found | 53.90 | 5.50 | 17.33 | 7.44 |

EXAMPLE 56

Preparation of 1-cyclopropyl-6-fluoro-8-chloro-7-(3-3S-methylaminopyrrolidin-1-yl)-3-(2,2-diethoxycarbonylacetyl)-1,4-dihydro-4-oxoquinoline hydrochloride 9.6 g of 1-cyclopropyl-6-fluoro-8-chloro-7-(3-N-methyl-3S-t-butoxycarbonylaminopyrrolidin-1-yl)-1,4-dihydro-4-oxoquinoline-3-carboxylic acid as a starting material was subjected to the same process as described in Example 20 to obtain 6.70 g of the object compound (yield: 60%).

Elementary analysis for $C_{25}H_{30}Cl_2FN_3O_6$

|            | C (%) | H (%) | O (%) | N (%) |
|------------|-------|-------|-------|-------|
| Calculated | 53.77 | 5.41  | 17.19 | 7.52  |
| Found      | 53.91 | 5.48  | 17.30 | 7.40  |

EXAMPLE 57

Preparation of 1-cyclopropyl-6-fluoro-8-chloro-7-(3-methylaminopyrrolidin-1-yl)-3-(2,2-diethoxycarbonylacetyl)-1,4-dihydro-4-oxoquinoline hydrochloride 9.6 g of 1-cyclopropyl-6-fluoro-8-chloro-7-(3-N-methyl-t-butoxycarbonylaminopyrrolidin-1-yl)-1,4-dihydro-4-oxoquinoline-3-carboxylic acid as a starting material was subjected to the same process as described in Example 20 to obtain 6.14 g of the object compound (yield: 55%).

Elementary analysis for $C_{25}H_{30}Cl_2FN_3O_6$

|            | C (%) | H (%) | O (%) | N (%) |
|------------|-------|-------|-------|-------|
| Calculated | 53.77 | 5.41  | 17.19 | 7.52  |
| Found      | 53.80 | 5.51  | 17.37 | 7.48  |

EXAMPLE 58

Preparation of 1-cyclopropyl-6-fluoro-8-methoxy-7-(3-3R-methylaminopyrrolidin-1-yl)-3-(2,2-diethoxycarbonylacetyl)-1,4-dihydro-4-oxoquinoline hydrochloride 9.51 g of 1-cyclopropyl-6-fluoro-8-methoxy-7-(3-N-methyl-3R-t-butoxycarbonylaminopyrrolidin-1-yl)-1,4-dihydro-4-oxoquinoline-3-carboxylic acid as a starting material was subjected to the same process as described in Example 20 to obtain 6.87 g of the object compound (yield: 62%).

Elementary analysis for $C_{26}H_{33}ClFN_3O_7$

|            | C (%) | H (%) | O (%) | N (%) |
|------------|-------|-------|-------|-------|
| Calculated | 56.37 | 6.00  | 20.22 | 7.58  |
| Found      | 56.50 | 6.11  | 20.35 | 7.49  |

EXAMPLE 59

Preparation of 1-cyclopropyl-6-fluoro-8-methoxy-7-(3-3S-methylaminopyrrolidin-1-yl)-3-(2,2-diethoxycarbonylacetyl)-1,4-dihydro-4-oxoquinoline hydrochloride 9.51 g of 1-cyclopropyl-6-fluoro-8-methoxy-7-(3-N-methyl-3S-t-butoxycarbonylaminopyrrolidin-1-yl)-1,4-dihydro-4-oxoquinoline-3-carboxylic acid as a starting material was subjected to the same process as described in Example 20 to obtain 6.43 g of the object compound (yield: 58%).

Elementary analysis for $C_{26}H_{33}ClFN_3O_7$

|            | C (%) | H (%) | O (%) | N (%) |
|------------|-------|-------|-------|-------|
| Calculated | 56.37 | 6.00  | 20.22 | 7.58  |
| Found      | 56.43 | 6.09  | 20.31 | 7.44  |

EXAMPLE 60

Preparation of 1-cyclopropyl-6-fluoro-8-methoxy-7-(3-methylaminopyrrolidin-1-yl)-3-(2,2-diethoxycarbonylacetyl)-1,4-dihydro-4-oxoquinoline hydrochloride 9.51 g of 1-cyclopropyl-6-fluoro-8-methoxy-7-(3-N-methyl-t-butoxycarbonylaminopyrrolidin-1-yl)-1,4-dihydro-4-oxoquinoline-3-carboxylic acid as a starting material was subjected to the same process as described in Example 20 to obtain 7.31 g of the object compound (yield: 66%).

Elementary analysis for $C_{26}H_{33}ClFN_3O_7$

|            | C (%) | H (%) | O (%) | N (%) |
|------------|-------|-------|-------|-------|
| Calculated | 56.37 | 6.00  | 20.22 | 7.58  |
| Found      | 56.55 | 6.07  | 20.30 | 7.43  |

EXAMPLE 61

Preparation of 1-cyclopropyl-6-fluoro-8-chloro-7-(3-3R-methylaminopyrrolidin-1-yl)-3-(2-nitroacetyl)-1,4-dihydro-4-oxoquinoline hydrochloride 9.6 g of 1-cyclopropyl-6-fluoro-8-chloro-7-(3-N-methyl-3R-t-butoxycarbonylaminopyrrolidin-1-yl)-1,4-dihydro-4-oxoquinoline-3-carboxylic acid as a starting material was subjected to the same processes as described in Examples 2 to 4 to obtain 5.79 g of the object compound (yield: 63%).

Elementary analysis for $C_{19}H_{21}Cl_2FN_4O_4$

|            | C (%) | H (%) | O (%) | N (%) |
|------------|-------|-------|-------|-------|
| Calculated | 49.69 | 4.61  | 13.93 | 12.20 |
| Found      | 49.81 | 4.66  | 14.09 | 12.11 |

EXAMPLE 62

Preparation of 1-cyclopropyl-6-fluoro-8-chloro-7-(3-3S-methylaminopyrrolidin-1-yl)-3-(2-nitroacetyl)-1,4-dihydro-4-oxoquinoline hydrochloride 9.6 g of 1-cyclopropyl-6-fluoro-8-chloro-7-(3-N-methyl-3S-t-butoxycarbonylaminopyrrolidin-1-yl)-1,4-dihydro-4-oxoquinoline-3-carboxylic acid as a starting material was subjected to the same processes as described in Examples 2 to 4 to obtain 5.33 g of the object compound (yield: 58%).

Elementary analysis for $C_{19}H_{21}Cl_2FN_4O_4$

| | C (%) | H (%) | O (%) | N (%) |
|---|---|---|---|---|
| Calculated | 49.69 | 4.61 | 13.93 | 12.20 |
| Found | 49.77 | 4.66 | 14.14 | 12.08 |

EXAMPLE 63

Preparation of 1-cyclopropyl-6-fluoro-8-chloro-7-(3-methylaminopyrrolidin-1-yl)-3-(2-nitroacetyl)-1,4-dihydro-4-oxoquinoline hydrochloride 9.6 g of 1-cyclopropyl-6-fluoro-8-chloro-7-(3-N-methyl-t-butoxycarbonylaminopyrrolidin-1-yl)-1,4-dihydro-4-oxoquinoline-3-carboxylic acid as a starting material was subjected to the same processes as described in Examples 2 to 4 to obtain 5.5 g of the object compound (yield: 60% ).

Elementary analysis for $C_{19}H_{21}Cl_2FN_4O_4$

| | C (%) | H (%) | O (%) | N (%) |
|---|---|---|---|---|
| Calculated | 49.69 | 4.61 | 13.93 | 12.20 |
| Found | 49.80 | 4.70 | 14.11 | 12.00 |

EXAMPLE 64

Preparation of 1-cyclopropyl-6-fluoro-8-methoxy-7-(3-3R-methylaminopyrrolidin-1-yl)-3-(2-nitroacetyl)-1,4-dihydro-4-oxoquinoline hydrochloride 9.51 g of 1-cyclopropyl-6-fluoro-8-methoxy-7-(3-N-methyl-3R-t-butoxycarbonylaminopyrrolidin-1-yl)-1,4-dihydro-4-oxoquinoline-3-carboxylic acid as a starting material was subjected to the same processes as described in Examples 2 to 4 to obtain 5.00 g of the object compound (yield: 55%).

Elementary analysis for $C_{20}H_{24}ClFN_4O_5$

| | C (%) | H (%) | O (%) | N (%) |
|---|---|---|---|---|
| Calculated | 52.81 | 5.32 | 17.59 | 12.32 |
| Found | 52.99 | 5.40 | 17.68 | 12.20 |

EXAMPLE 65

Preparation of 1-cyclopropyl-6-fluoro-8-methoxy-7-(3-3S-methylaminopyrrolidin-1-yl)-3-(2-nitroacetyl)-1,4-dihydro-4-oxoquinoline hydrochloride 9.51 g of 1-cyclopropyl-6-fluoro-8-methoxy-7-(3-N-methyl-3S-t-butoxycarbonylaminopyrrolidin-1-yl)-1,4-dihydro-4-oxoquinoline-3-carboxylic acid as a starting material was subjected to the same processes as described in Examples 2 to 4 to obtain 4.64 g of the object compound (yield: 51%).

Elementary analysis for $C_{20}H_{24}ClFN_4O_5$

| | C (%) | H (%) | O (%) | N (%) |
|---|---|---|---|---|
| Calculated | 52.81 | 5.32 | 17.59 | 12.32 |
| Found | 53.03 | 5.39 | 17.77 | 12.19 |

EXAMPLE 66

Preparation of 1-cyclopropyl-6-fluoro-8-methoxy-7-(3-methylaminopyrrolidin-1-yl)-3-(2-nitroacetyl)-1,4-dihydro-4-oxoquinoline hydrochloride 9.51 g of 1-cyclopropyl-6-fluoro-8-methoxy-7-(3-N-methyl-t-butoxycarbonylaminopyrrolidin-1-yl)-1,4-dihydro-4-oxoquinoline-3-carboxylic acid as a starting material was subjected to the same processes as described in Examples 2 to 4 to obtain 5.28 g of the object compound (yield: 58%).

Elementary analysis for $C_{20}H_{24}ClFN_4O_5$

| | C (%) | H (%) | O (%) | N (%) |
|---|---|---|---|---|
| Calculated | 52.81 | 5.32 | 17.59 | 12.32 |
| Found | 52.93 | 5.44 | 17.72 | 12.11 |

EXAMPLE 67

Preparation of organic or inorganic acid addition salts.

The compounds prepared in the above Examples were dissolved in water, and then the pH of this solution was adjusted to about 7 to precipitate the solid. The resulting solid was filtered, dried, and then dissolved in a mixture of chloroform-methanol. Various organic acids such as lactic acid, ascorbic acid, maleic acid, malonic acid, glutamic acid, citric acid, fumaric acid, p-toluenesulfonic acid, acetic acid, trifluoroacetic acid, propionic acid, tartaric acid, succinic acid or methanesulfonic acid, or inorganic acids such as sulfuric acid, nitric acid or the like were added to the above solution in the ratio of equivalent, and then the solvent was removed to give various acid addition salts.

The novel quinoline antibiotics of the present invention may be formulated in the form of injection or oral preparation. The examples of these preparations are as follows:

FORMULATION

Example I

A capsule formulation was prepared in accordance with the following composition:

| Component | Amount |
|---|---|
| Compound prepared in Example 56 | 100.0 mg |
| Corn starch | 25.0 mg |
| Calcium carboxymethyl cellulose | 23.0 mg |
| Magnesium stearate | 2.0 mg |
| Total | 150.0 mg |

Example II

A solution formulation was prepared in accordance with the following composition:

| Component | Amount |
|---|---|
| Compound prepared in Example 56 | 1 to 10 g |
| Lactic acid or Sodium hydroxide | 0.1 to 2 g |
| Mannitol | 0.1 g |
| Deionized water | 87.9 to 98.8 g |
| Total | 100 g |

The compounds prepared in the Examples were tested as follows:

1. In Vitro Antibacterial Activity Test

The antibacterial activities of the compounds of the present invention are shown in Table 1.

TABLE 1

In Vitro Anti-Bacterial Activity Test (MIC, μg/ml)

| | Example 4 | Example 5 | Example 6 | Example 7 | Example 8 | Example 9 | Example 10 | Example 11 |
|---|---|---|---|---|---|---|---|---|
| *Streptococcus pyogenes* 308A | 3.125 | 3.125 | 3.125 | 1.563 | 0.781 | 0.195 | 1.563 | 0.195 |
| *Streptococcus pyogenes* 77A | 0.781 | 0.781 | 0.781 | 0.781 | 0.195 | 0.195 | 0.781 | 0.098 |
| *Streptococcus faecium* MD8b | 0.781 | 0.781 | 0.781 | 0.781 | 0.391 | 0.195 | 1.563 | 0.098 |
| *Staphylococcus aureus* SG511 | 0.195 | 0.195 | 0.098 | 0.391 | 0.049 | 0.025 | 0.391 | 0.013 |
| *Staphylococcus aureus* 285 | 0.391 | 0.195 | 0.195 | 0.391 | 0.025 | 0.025 | 0.391 | 0.025 |
| *Staphylococcus aureus* 503 | 0.781 | 0.781 | 0.391 | 0.391 | 0.025 | 0.013 | 0.391 | 0.025 |
| *Escherichia coli* 078 | <0.002 | <0.002 | <0.002 | 0.049 | 0.007 | 0.007 | 0.049 | <0.002 |
| *Escherichia coli* DC0 | 0.195 | 0.195 | 0.195 | 0.391 | 0.195 | 0.195 | 1.563 | 0.049 |
| *Escherichia coli* DC2 | 0.391 | 0.391 | 0.098 | 0.391 | 0.013 | 0.025 | 0.391 | 0.013 |
| *Escherichia coil* TEM | 0.013 | 0.007 | <0.002 | 0.195 | <0.002 | <0.002 | 0.098 | <0.002 |
| *Escherichia coli* 1507E | 0.007 | 0.013 | <0.002 | 0.025 | 0.007 | 0.013 | 0.098 | <0.002 |
| *Pseudomonas aeruginosa* 9027 | 0.195 | 0.195 | 0.391 | 0.781 | 0.391 | 0.391 | 3.125 | 0.195 |
| *Pseudomonas aeruginosa* 1592E | 0.195 | 0.195 | 0.195 | 0.781 | 0.195 | 0.098 | 1.563 | 0.195 |
| *Pseudomonas aeruginosa* 1771 | 0.195 | 0.195 | 0.195 | 1.563 | 0.391 | 0.195 | 3.125 | 0.098 |
| *Pseudomonas aeruginosa* 1771M | 0.098 | 0.049 | 0.049 | 0.391 | 0.049 | 0.049 | 1.563 | 0.025 |
| *Salmonella typhimurium* | 0.007 | 0.007 | <0.002 | 0.098 | 0.007 | 0.007 | 0.049 | <0.002 |
| *Klebsiella oxytoca* 1082E | <0.002 | <0.002 | <0.002 | <0.002 | <0.002 | <0.002 | 0.025 | <0.002 |
| *Klebsiella aerogenes* 1522E | 0.013 | 0.025 | 0.007 | 0.391 | 0.007 | 0.004 | 1.563 | 0.007 |
| *Enterobacter cloacae* P99 | 0.007 | 0.007 | <0.002 | 0.391 | <0.002 | <0.002 | 0.049 | <0.002 |
| *Enterobacter cloacae* 1321E | <0.002 | <0.002 | <0.002 | 0.013 | <0.002 | 0.007 | 0.049 | <0.002 |

| | Example 12 | Example 13 | Example 14 | Example 15 | Example 16 | Example 18 | Example 19 | Example 20 |
|---|---|---|---|---|---|---|---|---|
| *Streptococcus pyogenes* 308A | 0.391 | 0.195 | 1.563 | 0.049 | 0.098 | 3.125 | 3.125 | 0.391 |
| *Streptococcus pyogenes* 77A | 0.195 | 0.195 | 0.195 | 0.025 | 0.025 | 0.781 | 1.563 | 0.098 |
| *Streptococcus faecium* MD8b | 0.098 | 0.195 | 0.391 | 0.025 | 0.013 | 0.781 | 0.781 | 0.098 |
| *Staphylococcus aureus* SG511 | 0.025 | 0.025 | 0.098 | <0.002 | 0.004 | 0.195 | 0.391 | 0.013 |
| *Staphylococcus aureus* 285 | 0.025 | 0.025 | 0.098 | 0.004 | 0.004 | 0.391 | 1.563 | 0.013 |
| *Staphylococcus aureus* 503 | 0.025 | 0.049 | 0.049 | <0.002 | <0.002 | 0.391 | 0.781 | 0.025 |
| *Escherichia coli* 078 | <0.002 | <0.002 | <0.002 | <0.002 | 0.004 | 0.004 | 0.004 | <0.002 |
| *Escherichia coli* DC0 | 0.098 | 0.049 | 0.098 | 0.098 | 0.098 | 0.195 | 0.391 | 0.098 |
| *Escherichia coli* DC2 | 0.049 | 0.013 | 0.049 | 0.013 | 0.013 | 0.098 | 0.391 | 0.013 |
| *Escherichia coli* TEM | 0.004 | <0.002 | 0.007 | 0.004 | 0.004 | 0.007 | 0.195 | <0.002 |
| *Escherichia coli* 1507E | 0.004 | 0.004 | 0.013 | 0.007 | 0.013 | 0.004 | 0.013 | 0.007 |
| *Pseudomonas aeruginosa* 9027 | 0.391 | 0.195 | 0.781 | 0.781 | 0.781 | 0.781 | 0.781 | 0.391 |
| *Pseudomonas aeruginosa* 1592E | 0.391 | 0.195 | 0.781 | 0.391 | 0.781 | 0.391 | 1.563 | 0.195 |
| *Pseudomonas aeruginosa* 1771 | 0.195 | 0.195 | 0.391 | 0.391 | 0.391 | 0.195 | 0.781 | 0.195 |
| *Pseudomonas aeruginosa* 1771M | 0.049 | 0.049 | 0.195 | 0.195 | 0.195 | 0.049 | 1.563 | 0.098 |
| *Salmonella typhimurium* | <0.002 | <0.002 | <0.002 | <0.002 | <0.02 | 0.007 | 0.391 | <0.002 |
| *Klebsiella oxytoca* 1082E | <0.002 | <0.002 | <0.002 | <0.002 | 0.007 | 0.004 | 0.013 | <0.002 |
| *Klebsiella aerogenes* 1522E | 0.025 | 0.013 | 0.025 | 0.013 | 0.013 | 0.013 | 0.049 | 0.025 |
| *Enterobacter cloacae* P99 | 0.004 | 0.004 | 0.007 | 0.004 | 0.007 | <0.002 | 0.013 | <0.002 |
| *Enterobacter cloacae* 1321E | <0.002 | <0.002 | <0.002 | <0.002 | 0.007 | <0.002 | 0.013 | <0.002 |

| | Example 21 | Example 22 | Example 23 | Example 24 | Example 25 | Example 26 | Example 27 | Example 28 |
|---|---|---|---|---|---|---|---|---|
| *Streptococcus pyogenes* 308A | 0.781 | 0.391 | 0.781 | 0.391 | 0.781 | 1.563 | 0.781 | 0.098 |
| *Streptococcus pyogenes* 77A | 0.391 | 0.781 | 0.195 | 0.391 | 0.391 | 0.781 | 0.391 | 0.049 |
| *Streptococcus faecium* MD8b | 0.781 | 0.391 | 0.195 | 0.391 | 0.391 | 0.781 | 0.391 | 0.049 |
| *Staphylococcus aureus* SG511 | 0.049 | 0.049 | 0.049 | 0.049 | 0.098 | 0.098 | 0.098 | 0.004 |
| *Staphylococcus aureus* 285 | 0.049 | 0.098 | 0.049 | 0.049 | 0.049 | 0.098 | 0.049 | 0.007 |
| *Staphylococcus aureus* 503 | 0.049 | 0.049 | 0.049 | 0.049 | 0.049 | 0.098 | 0.049 | <0.002 |
| *Escherichia coli* 078 | 0.004 | 0.004 | <0.002 | <0.002 | <0.002 | 0.004 | 0.004 | <0.002 |
| *Escherichia coli* DC0 | 0.098 | 0.098 | 0.195 | 0.098 | 0.098 | 0.195 | 0.098 | 0.195 |
| *Escherichia coli* DC2 | 0.049 | 0.025 | 0.049 | 0.025 | 0.025 | 0.098 | 0.013 | 0.049 |
| *Escherichia coli* TEM | 0.013 | <0.002 | 0.004 | <0.002 | <0.002 | 0.013 | <0.002 | 0.013 |
| *Escherichia coli* 1507E | 0.013 | <0.002 | 0.013 | <0.002 | 0.025 | 0.025 | 0.013 | 0.013 |
| *Pseudomonas aeruginosa* 9027 | 0.391 | 0.781 | 0.781 | 0.391 | 0.391 | 0.781 | 0.391 | 0.781 |
| *Pseudomonas aeruginosa* 1592E | 0.391 | 0.781 | 0.391 | 0.391 | 0.195 | 0.781 | 0.195 | 0.391 |
| *Pseudomonas aeruginosa* 1771 | 0.195 | 0.781 | 0.391 | 0.391 | 0.195 | 0.781 | 0.195 | 0.781 |
| *Pseudomonas aeruginosa* 1771M | 0.098 | 0.195 | 0.098 | 0.049 | 0.098 | 0.098 | 0.098 | 0.195 |
| *Salmonella typhimurium* | 0.013 | 0.004 | 0.004 | <0.002 | 0.004 | 0.007 | <0.002 | 0.013 |
| *Klebsiella oxytoca* 1082E | 0.004 | <0.002 | <0.002 | <0.002 | <0.002 | <0.002 | <0.002 | 0.007 |
| *Klebsiella aerogenes* 1522E | 0.025 | 0.025 | 0.025 | 0.013 | 0.013 | 0.049 | 0.013 | 0.013 |
| *Enterobacter cloacae* P99 | 0.007 | 0.004 | 0.004 | <0.002 | 0.004 | 0.013 | 0.004 | <0.002 |
| *Enterobacter cloacae* 1321E | <0.002 | <0.002 | <0.002 | <0.002 | <0.002 | 0.004 | <0.002 | <0.002 |

| | Example 29 | Example 30 | Example 31 | Example 33 | Example 34 | Example 35 | Example 36 | Example 37 |
|---|---|---|---|---|---|---|---|---|
| *Streptococcus pyogenes* 308A | 0.391 | 1.563 | 3.125 | 3.125 | 0.391 | 0.195 | 0.391 | 1.563 |
| *Streptococcus pyogenes* 77A | 0.098 | 1.563 | 1.563 | 3.125 | 0.098 | 0.098 | 0.098 | 3.125 |
| *Streptococcus faecium* MD8b | 0.098 | 1.563 | 0.781 | 6.25 | 0.098 | 0.098 | 0.195 | 3.125 |
| *Staphylococcus aureus* SG511 | 0.013 | 0.195 | 0.781 | 1.563 | 0.025 | 0.025 | 0.025 | 0.781 |
| *Staphylococcus aureus* 285 | 0.049 | 0.195 | 0.391 | 1.563 | 0.049 | 0.025 | 0.049 | 0.781 |
| *Staphylococcus aureus* 503 | 0.013 | 0.195 | 0.391 | 0.781 | 0.098 | 0.013 | 0.049 | 0.781 |
| *Escherichia coli* 078 | 0.013 | 0.049 | 0.391 | 0.195 | <0.002 | 0.007 | 0.007 | 0.391 |
| *Escherichia coli* DC0 | 0.195 | 0.781 | 0.195 | 0.195 | 0.195 | 0.098 | 0.195 | 0.781 |

TABLE 1-continued

In Vitro Anti-Bacterial Activity Test (MIC, µg/ml)

| | | | | | | | | |
|---|---|---|---|---|---|---|---|---|
| *Escherichia coli* DC2 | 0.098 | 0.195 | 0.391 | 0.098 | 0.098 | 0.049 | 0.049 | 0.391 |
| *Escherichia coli* TEM | 0.013 | 0.391 | 0.195 | 0.098 | 0.007 | 0.013 | 0.025 | 0.098 |
| *Escherichia coli* 1507E | 0.049 | 0.391 | 0.198 | 0.195 | 0.007 | 0.007 | 0.025 | 0.195 |
| *Pseudomonas aeruginosa* 9027 | 1.563 | 0.781 | 0.781 | 1.563 | 0.391 | 0.781 | 1.563 | 1.563 |
| *Pseudomonas aeruginosa* 1592E | 0.781 | 0.781 | 0.781 | 1.563 | 0.391 | 0.781 | 0.781 | 3.125 |
| *Pseudomonas aeruginosa* 1771 | 1.563 | 0.391 | 0.781 | 1.563 | 0.195 | 0.391 | 0.781 | 1.563 |
| *Pseudomonas aeruginosa* 1771M | 0.391 | 0.195 | 0.391 | 0.781 | 0.098 | 0.098 | 0.195 | 0.781 |
| *Salmonella typhimurium* | 0.391 | 0.781 | 0.391 | 0.781 | 0.004 | 0.013 | 0.025 | 0.195 |
| *Klebsiella oxytoca* 1082E | 0.049 | 0.391 | 0.195 | 0.391 | <0.002 | <0.002 | 0.007 | 0.195 |
| *Klebsiella aerogenes* 1522E | 0.013 | 0.098 | 0.098 | 0.391 | 0.013 | 0.013 | 0.025 | 0.391 |
| *Enterobacter cloacae* P99 | 0.013 | 0.049 | 0.098 | 0.195 | 0.007 | 0.025 | 0.025 | 0.195 |
| *Enterobacter cloacae* 1321E | 0.007 | 0.049 | 0.049 | 0.098 | 0.049 | 0.025 | 0.025 | 0.195 |

| | Example 38 | Example 39 | Example 40 | Example 41 | Example 42 | Example 43 | Example 44 | Example 45 |
|---|---|---|---|---|---|---|---|---|
| *Streptococcus pyogenes* 308A | 1.563 | 25 | 25 | 25 | 25 | 25 | 25 | 25 |
| *Streptococcus pyogenes* 77A | 0.781 | 6.25 | 12.5 | 12.5 | 12.5 | 25 | 25 | 25 |
| *Streptococcus faecium* MD8b | 0.781 | 6.25 | 12.5 | 25 | 12.5 | 12.5 | 25 | 6.25 |
| *Staphylococcus aureus* SG511 | 0.391 | 1.563 | 1.563 | 3.125 | 6.25 | 3.125 | 6.25 | 0.781 |
| *Staphylococcus aureus* 285 | 0.781 | 1.563 | 3.125 | 6.25 | 3.125 | 3.125 | 6.25 | 1.563 |
| *Staphylococcus aureus* 503 | 0.391 | 1.563 | 1.563 | 6.25 | 3.125 | 0.195 | 6.25 | 1.563 |
| *Escherichia coli* 078 | 0.195 | 0.049 | 0.098 | 0.049 | 0.098 | 6.25 | 0.195 | 0.049 |
| *Escherichia coli* DC0 | 0.195 | 6.25 | 6.25 | 3.125 | 12.5 | 3.125 | 3.125 | 1.563 |
| *Escherichia coli* DC2 | 0.098 | 3.125 | 3.125 | 1.563 | 3.125 | 1.563 | 1.563 | 0.781 |
| *Escherichia coli* TEM | 0.195 | 0.391 | 0.391 | 0.195 | 0.781 | 1.563 | 0.391 | 0.195 |
| *Escherichia coli* 1507E | 0.098 | 0.781 | 0.781 | 0.391 | 0.195 | 12.5 | 0.781 | 0.195 |
| *Pseudomonas aeruginosa* 9027 | 1.563 | 12.5 | 12.5 | 6.25 | 2.5 | 6.25 | 12.5 | 6.25 |
| *Pseudomonas aeruginosa* 1592E | 0.781 | 12.5 | 6.25 | 3.125 | 12.5 | 12.5 | 6.25 | 3.125 |
| *Pseudomonas aeruginosa* 1771 | 1.563 | 12.5 | 6.25 | 3.125 | 6.25 | 3.125 | 12.5 | 3.125 |
| *Pseudomonas aeruginosa* 1771M | 0.391 | 3.125 | 3.125 | 1.563 | 6.25 | 1.563 | 3.125 | 0.781 |
| *Salmonella typhimurium* | 0.049 | 0.391 | 0.195 | 0.098 | 1.563 | 0.195 | 0.195 | 0.098 |
| *Klebsiella oxytoca* 1082E | 0.025 | 0.049 | 0.049 | 0.049 | 0.098 | 0.098 | 0.195 | 0.049 |
| *Klebsiella aerogenes* 1522E | 0.098 | 0.781 | 0.391 | 0.195 | 1.563 | 0.781 | 0.391 | 0.391 |
| *Enterobacter cloacae* P99 | 0.098 | 0.391 | 0.391 | 0.098 | 0.781 | 0.391 | 0.195 | 0.195 |
| *Enterobacter cloacae* 1321E | 0.049 | 0.049 | 0.049 | 0.049 | 0.098 | 0.049 | 0.098 | 0.098 |

| | Example 46 | Example 47 | Example 48 | Example 49 | Example 50 | Example 51 | Example 52 | Example 53 |
|---|---|---|---|---|---|---|---|---|
| *Streptococcus pyogenes* 308A | 1.563 | 1.563 | 0.781 | 0.391 | 0.781 | 0.781 | 0.195 | 0.098 |
| *Streptococcus pyogenes* 77A | 0.391 | 0.781 | 0.391 | 0.098 | 0.391 | 0.391 | 0.391 | 0.049 |
| *Streptococcus faecium* MD8b | 0.195 | 0.781 | 0.195 | 0.195 | 0.195 | 0.391 | 0.391 | 0.049 |
| *Staphylococcus aureus* SG511 | 0.098 | 0.391 | 0.195 | 0.098 | 0.098 | 0.195 | 0.025 | 0.013 |
| *Staphylococcus aureus* 285 | 0.049 | 0.195 | 0.195 | 0.098 | 0.098 | 0.098 | 0.025 | 0.007 |
| *Staphylococcus aureus* 503 | 0.049 | 0.391 | 0.195 | 0.098 | 0.098 | 0.098 | 0.025 | 0.013 |
| *Escherichia coli* 078 | 0.025 | 0.195 | 0.049 | 0.049 | 0.025 | 0.025 | 0.007 | <0.002 |
| *Escherichia coli* DC0 | 0.391 | 0.781 | 0.391 | 0.391 | 0.195 | 0.781 | 0.049 | 0.195 |
| *Escherichia coli* DC2 | 0.098 | 0.391 | 0.098 | 0.098 | 0.049 | 0.195 | 0.025 | 0.049 |
| *Escherichia coli* TEM | 0.049 | 0.195 | 0.049 | 0.049 | 0.049 | 0.049 | <0.002 | 0.013 |
| *Escherichia coli* 1507E | 0.098 | 0.391 | 0.195 | 0.098 | 0.098 | 0.049 | 0.004 | 0.025 |
| *Pseudomonas aeruginosa* 9027 | 1.563 | 1.563 | 3.125 | 3.125 | 1.563 | 0.781 | 0.781 | 0.781 |
| *Pseudomonas aeruginosa* 1592E | 0.781 | 0.781 | 1.563 | 1.563 | 0.781 | 0.391 | 0.391 | 0.391 |
| *Pseudomonas aeruginosa* 1771 | 1.563 | 0.781 | 3.125 | 3.125 | 1.563 | 0.781 | 0.391 | 0.781 |
| *Pseudomonas aeruginosa* 1771M | 0.195 | 0.195 | 0.781 | 0.781 | 0.391 | 0.195 | 0.098 | 0.195 |
| *Salmonella typhimurium* | 0.195 | 0.098 | 0.391 | 0.049 | 0.013 | 0.025 | 0.013 | 0.013 |
| *Klebsiella oxytoca* 1082E | 0.013 | 0.098 | 0.195 | 0.013 | 0.013 | 0.013 | <0.002 | <0.002 |
| *Klebsiella aerogenes* 1522E | 0.013 | 0.049 | 0.195 | 0.098 | 0.195 | 0.195 | 0.013 | 0.013 |
| *Enterobacter cloacae* P99 | 0.098 | 0.049 | 0.098 | 0.049 | 0.013 | 0.025 | 0.004 | 0.013 |
| *Enterobacter cloacae* 1321E | 0.049 | 0.049 | 0.098 | 0.025 | 0.013 | 0.025 | <0.002 | <0.002 |

| | Example 55 | Example 56 | Example 57 | Example 58 | Example 59 | Example 60 |
|---|---|---|---|---|---|---|
| *Streptococcus pyogenes* 308A | 1.563 | 0.781 | 0.781 | 1.563 | 0.781 | 1.563 |
| *Streptococcus pyogenes* 77A | 0.391 | 0.195 | 0.195 | 1.563 | 0.781 | 0.781 |
| *Streptococcus faecium* MD8b | 0.391 | 0.195 | 0.098 | 1.563 | 0.781 | 0.781 |
| *Staphylococcus aureus* SG511 | 0.098 | 0.049 | 0.049 | 0.195 | 0.098 | 0.195 |
| *Staphylococcus aureus* 285 | 0.195 | 0.098 | 0.195 | 0.195 | 0.098 | 0.195 |
| *Staphylococcus aureus* 503 | 0.195 | 0.098 | 0.195 | 0.195 | 0.098 | 0.098 |
| *Escherichia coli* 078 | 0.013 | 0.007 | 0.007 | 0.098 | 0.049 | 0.098 |
| *Escherichia coli* DC0 | 0.391 | 0.195 | 0.049 | 1.563 | 0.781 | 0.781 |
| *Escherichia coli* DC2 | 0.098 | 0.049 | 0.025 | 0.195 | 0.098 | 0.098 |
| *Escherichia coli* TEM | 0.025 | 0.013 | 0.013 | 0.098 | 0.049 | 0.098 |
| *Escherichia coli* 1507E | 0.025 | 0.013 | 0.013 | 0.391 | 0.391 | 0.195 |
| *Pseudomonas aeruginosa* 9027 | 1.563 | 0.781 | 1.563 | 1.563 | 1.563 | 1.563 |
| *Pseudomonas aeruginosa* 1592E | 0.391 | 0.391 | 0.781 | 1.563 | 1.563 | 1.563 |
| *Pseudomonas aeruginosa* 1771 | 0.391 | 0.391 | 0.391 | 1.563 | 1.563 | 1.563 |
| *Pseudomonas aeruginosa* 1771M | 0.195 | 0.098 | 0.195 | 0.781 | 0.781 | 0.781 |
| *Salmonella typhimurium* | 0.013 | 0.007 | 0.013 | 0.195 | 0.049 | 0.098 |
| *Klebsiella oxytoca* 1082E | 0.025 | 0.013 | 0.049 | 0.049 | 0.007 | 0.013 |
| *Klebsiella aerogenes* 1522E | 0.049 | 0.049 | 0.049 | 0.195 | 0.098 | 0.195 |
| *Enterobacter cloacae* P99 | 0.025 | 0.013 | 0.013 | 0.098 | 0.049 | 0.098 |
| *Enterobacter cloacae* 1321E | 0.049 | 0.049 | 0.049 | 0.098 | 0.049 | 0.098 |

| | Example 61 | Example 62 | Example 63 | Example 64 | Example 65 | Example 66 |
|---|---|---|---|---|---|---|
| *Streptococcus pyogenes* 308A | 0.391 | 0.098 | 0.391 | 0.781 | 0.781 | 1.563 |

TABLE 1-continued

In Vitro Anti-Bacterial Activity Test (MIC, μg/ml)

| | | | | | | |
|---|---|---|---|---|---|---|
| Streptococcus pyogenes 77A | 0.098 | 0.049 | 0.098 | 0.781 | 0.781 | 0.781 |
| Streptococcus faecium MD8b | 0.098 | 0.049 | 0.098 | 0.391 | 0.781 | 0.781 |
| Staphylococcus aureus SG511 | 0.013 | 0.013 | 0.025 | 0.391 | 0.049 | 0.391 |
| Staphylococcus aureus 285 | 0.025 | 0.025 | 0.049 | 0.098 | 0.049 | 0.391 |
| Staphylococcus aureus 503 | 0.025 | 0.013 | 0.049 | 0.098 | 0.098 | 0.098 |
| Escherichia coli 078 | <0.002 | <0.002 | <0.002 | 0.049 | 0.049 | 0.098 |
| Escherichia coli DC0 | 0.049 | 0.025 | 0.098 | 0.391 | 0.781 | 0.781 |
| Escherichia coli DC2 | 0.013 | 0.013 | 0.025 | 0.049 | 0.195 | 0.195 |
| Escherichia coli TEM | 0.007 | 0.007 | 0.007 | 0.049 | 0.049 | 0.195 |
| Escherichia coli 1507E | 0.007 | 0.007 | 0.007 | 0.098 | 0.195 | 0.391 |
| Pseudomonas aeruginosa 9027 | 0.195 | 0.195 | 0.391 | 1.563 | 1.563 | 1.563 |
| Pseudomonas aeruginosa 1592E | 0.195 | 0.098 | 0.195 | 1.563 | 1.563 | 1.563 |
| Pseudomonas aeruginosa 1771 | 0.195 | 0.098 | 0.195 | 0.781 | 1.563 | 1.563 |
| Pseudomonas aeruginosa 1771M | 0.098 | 0.098 | 0.049 | 0.781 | 1.563 | 1.563 |
| Salmonella typhimurium | 0.004 | 0.025 | 0.004 | 0.013 | 0.781 | 0.781 |
| Klebsiella oxytoca 1082E | 0.004 | <0.002 | 0.007 | 0.007 | 0.049 | 0.098 |
| Klebsiella aerogenes 1522E | 0.013 | 0.007 | 0.013 | 0.098 | 0.049 | 0.013 |
| Enterobacter cloacae P99 | 0.007 | 0.007 | 0.013 | 0.049 | 0.013 | 0.195 |
| Enterobacter cloacae 1321E | 0.007 | 0.007 | 0.013 | 0.049 | 0.013 | 0.049 |

The above in vitro antibacterial activity test was carried out in accordance with the agar culture medium dilution method (Hoechst 345) by using Muller-Hinton agar medium to determine the minimum inhibitory concentration (MIC).

The strains having $10^7$ C.F.U./ml were inoculated on the culture medium, and the growth of the strains was observed after incubating them at 37° C. for 18 hours, in which ciprofloxacin was used as a control antibacterial agent. In this test, twenty typical strains were used.

2. Treatment Effect on the Systemic Infection 10 fold of the pathogens which lead to 100% lethality were injected intraperitoneally to male and female NMRI mice weighing 18 to 20 g. Immediately and 4 hours after injection, the dose of test compounds, which was determined by two-fold serial dilution method, was administered orally or subcutaneously to the mice, and on the 10th day, the effect was evaluated in terms of $ED_{50}$ calculated from the number of survived mice by the probit analysis. The results of the test are shown in Table 2.

TABLE 2

Treatment Effect on the Systemic Infection

| | | $ED_{50}$:mg/kg | |
|---|---|---|---|
| Pathogens | Compound | Subcutaneous Injection | Oral Administration |
| S. aureus 17740 | Example 13 | 16.8 | 127.7 |
| | Example 16 | 97.6 | 49.7 |
| | Ofloxacin | 200.0 | >200.0 |
| | Ciprofloxacin | 132.3 | >200.0 |
| P. mirabilis | Example 13 | 0.08 | 0.21 |
| | Example 34 | 0.16 | 0.41 |
| | Ofloxacin | 0.33 | 1.64 |
| | Ciprofloxacin | 0.16 | 0.82 |

3. Acute Toxicity Test

Test compounds were administered to ICR mice weighing 20 to 25 g. On 14th day, $LD_{50}$ was calculated from the number of survived mice by the probit analysis. The results of the test are shown in Table 3.

TABLE 3

Acute Toxicity Test

| | Acute Toxicity ($LD_{50}$:mg/kg) | |
|---|---|---|
| Compound | Peritomeo Injection | Oral Administration |
| Example 13 | 580 | 3800 |

TABLE 3-continued

Acute Toxicity Test

| | Acute Toxicity ($LD_{50}$:mg/kg) | |
|---|---|---|
| Compound | Peritomeo Injection | Oral Administration |
| Example 16 | 605 | 3800 |
| Example 34 | 620 | 4000 |

As can be seen from the above results, the compounds of the present invention possess a broad spectrum of potent antibacterial activity against gram-positive and gram-negative bacteria. The compounds of the present invention also exhibit an excellent activity in terms of 50% effective dose ($ED_{50}$) on the systemic bacterial infection. Further, it has been proved that the compounds of the present invention have a low toxicity sufficient to be useful as drugs as a result of the acute toxicity test and no effects on the cardiovascular system of the dogs, particularly blood pressure lowering effect.

Accordingly, the compounds of the present invention may be advantageously used as therapeutically active compounds and preservatives of inorganic and organic materials.

What is claimed is:

1. A quinoline compound of formula (I):

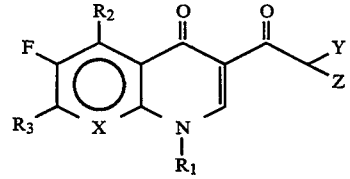

wherein:

$R_1$ is a straight chain alkyl group having 1 to 3 carbon atoms or a cyclopropyl group, a straight chain alkyl group having 1 to 3 carbon atoms or a cyclopropyl group which is substituted with a halogen atom, a phenyl group or a phenyl group substituted with one or two halogen atoms;

$R_2$ is a hydrogen atom, a lower alkyl or amino group;

$R_3$ is a halogen atom or a heterocyclic group represented by the following formula (A) which contains at least one nitrogen atom as a hereto atom in the ring;

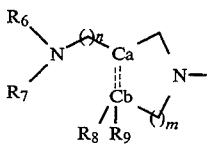

wherein:
R6, R7, R8 and R9 are each hydrogen atoms or lower alkyl groups, or two of these groups may form a bond, m and n are 0 or 1, and $C_a$══$C_b$ may not form a bond and $C_a$ is $CHR_{10}$ wherein $R_{10}$ is a hydrogen atom or a lower alkyl group; or $C_a$══$C_b$ form a single bond; or $C_a$══$C_b$ form a double bond in which case R9 is absent;

X is C—R4 wherein R4 is hydrogen or halogen atom, or lower alkyl or lower alkoxy group; and Y and Z are each hydrogen atoms, or electron withdrawing groups selected from carboxyester, cyano, nitro, acetyl or trifluoroacetyl, amide group, or lower alkysulfonyl group, provided that Y and Z are not simultaneously hydrogen atoms, or pharmaceutically acceptable acid addition salts thereof.

2. The compound of claim 1, wherein R1 is ethyl, cyclopropyl, 2-fluoroethyl or 2,4-difluorophenyl group; and R3 is piperazine, 3-methylpiperazine, 3,5-dimethylpiperazine, 3-aminopyrrolidine, 3-methylaminopyrrolidine, 3-aminomethylipyrrolidine, 3-methylaminomethyl-2,5-dihydropyrrole,

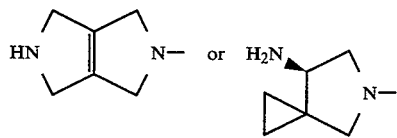

group.

3. The compound of claim 1, wherein the compound of formula (I) is one of the following compounds:

1-cyclopropyl-6-fluoro-7-(piperazin-1-yl)-3-(2-nitroacetyl)-1,4-dihydro-4-oxoquinoline hydrochloride;

1-cyclopropyl-6-fluoro-7-(piperazin-1-yl)-3-(2-nitroacetyl)-1,4-dihydro-4-oxoquinoline trifluoroacetate;

1-cyclopropyl-6,8-difluoro-7-(piperazin-1-yl)-3-(2-nitroacetyl)-1,4-dihydro-4-oxoquinoline hydrochloride;

1-cyclopropyl-6,8-difluoro-7-(3-methylpiperazin-1-yl)-3-(2-nitroacetyl)-1,4-dihydro-4-oxoquinoline-hydrochloride;

1-(2,4-difluorophenyl)-6-fluoro-7-(3-aminopyrrolidin-1-yl)-3-(2-nitroacetyl)-1,4-dihydro-4-oxoquinoline hydrochloride;

1-(2,4-difluorophenyl)-6-fluoro-7-(3-methylpiperazin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2-nitroacetyl)-1,4-dihydro-4-oxoquinoline hydrochloride;

1-cyclopropyl-6-fluoro-8-chloro-7-(3-3R-aminopyrrolidin-1-yl)-3-(2-nitroacetyl)-1,4-dihydro-4-oxoquinoline hydrochloride;

1-cyclopropyl-6-fluoro-8-chloro-7-(3-3S-aminopyrrolidin-1-yl)-3-(2-nitroacetyl)-1,4-dihydro-4-oxoquinoline hydrochloride;

1-cyclopropyl-5-amino-6,8-difluoro-7-(3,5-cis-dimethylpiperazin-1-yl)-3-(2-nitroacetyl)-1,4-dihydro-4-oxoquinoline hydrochloride;

1-cyclopropyl-6,8-difluoro-7-(3-methylaminomethyl-2,5-dihydropyrrol-1-yl)-3-(2-nitroacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-nitroacetyl)-1,4-dihydro-4-oxoquinoline hydrochloride;

1-cyclopropyl-6-fluoro-7-(piperazin-1-yl)-3-(2,2-diethoxycarbonylacetyl)-1,4-dihydro-4-oxoquinoline hydrochloride;

1-cyclopropyl-6-fluoro-7-(piperazin-1-yl)-3-(2-ethoxycarbonylacetyl)-1,4-dihydro-4-oxoquinoline hydrochloride;

1-cyclopropyl-6,8-difluoro-7-(3-aminopyrrolidin-1-yl)-3-(2,2-diethoxycarbonylacetyl)-1,4-dihydro-4-oxoquinoline hydrochloride;

1-cyclopropyl-6,8-difluoro-7-(3-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-3S-methylaminopyrrolidin-1-yl)-3-(2-nitroacetyl)-1,4-dihydro-4-oxoquinoline hydrochloride;

1-cyclopropyl-6-fluoro-8-chloro-7-(3-3R-methylaminopyrrolidin-1-yl)-3-(2-nitroacetyl)-1,4-dihydro-4-oxoquinoline hydrochloride;

1-cyclopropyl-6-fluoro-8-chloro-7-(3-methylaminopyrrolidin-1-yl)-3-(2-nitroacetyl)-1,4-dihydro-4-oxoquinoline hydrochloride;

1-cyclopropyl-6-fluoro-8-methoxy-7-(3-3S-methylaminopyrrolidin-1-yl)-3-(2-nitroacetyl)-1,4-dihydro-4-oxoquinoline hydrochloride;

1-cyclopropyl-6-fluoro-8-methoxy-7-(3-3R-methylaminopyrrolidin-1-yl)-3-(2-nitroacetyl)-1,4-dihydro-4-oxoquinoline hydrochloride;

1-cyclopropyl-6-fluoro-8-methoxy-7-(3-methylaminopyrrolidin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-3R-aminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-3S-aminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-3R-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-3S-aminopyrrolidin-1-yl)-3-(2-ethoxycarbonylacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2,2-diethoxycarbonylacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-ethoxycarbonylacetyl)-1,4-dihydro-4-oxoquinoline hydrochloride;

1-ethyl-6,8-difluoro-7-(3-aminopyrrolidin-1-yl)-3-(2-nitroacetyl)-1,4-dihydro-4-oxoquinoline hydrochloride;

1-cyclopropyl-6-fluoro-8-chloro-7-(3-3S-methylaminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-3R-methylaminopyrrolidin-1-yl)-3-(2,2-diethoxycarbonylacetyl)-1,4-dihydro-4-oxoquinoline hydrochloride;

1-cyclopropyl-6-fluoro-8-chloro-7-(3-methylaminopyrrolidin-1-yl)-3-(2,2-diethoxycarbonylacetyl)-1,4-dihydro-4-oxoquinoline hydrochloride;

1-cyclopropyl-6-fluoro-8-methoxy-7-(3-3S-methylaminopyrrolidin-1-yl)-3-(2,2-diethoxycarbonylacetyl)-1,4-dihydro-4-oxoquinoline hydrochloride;

1-cyclopropyl-6-fluoro-8-methoxy-7-(3-3R-methylaminopyrrolidin-1-yl)-3-(2,2-diethoxycarbonylacetyl)-1,4-dihydro-4-oxoquinoline hydrochloride;

1-cyclopropyl-6-fluoro-8-methoxy-7-(3-methylaminopyrrolidin-1-yl)-3-(2,2-diethoxycarbonylacetyl)-1,4-dihydro-4-oxoquinoline hydrochloride;

1-(2-fluoroethyl)-6,8-difluoro-7-(3-aminopyrrolidin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2-methanesulfonylacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2-nitroacetyl)-1,4-dihydro-4-oxoquinoline hydrochloride;

1-cyclopropyl-6-fluoro-8-chloro-7-(7-amino-5-azaspiro[2.4]hept-5-yl)-3-(2-nitroacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2,2-diethoxycarbonylacetyl)-1,4-dihydro-4-oxoquinoline hydrochloride;

1-cyclopropyl-6-fluoro-8-chloro-7-(3-aminopyrrolidin-1-yl)-3-(2-acetoacetyl)-1,4-dihydro-4-oxoquinoline hydrochloride;

1-cyclopropyl-6-fluoro-8-chloro-7-(3-aminopyrrolidin-1-yl)-3-(2-trifluoroacetoacetyl)-1,4-dihydro-4-oxoquinoline hydrochloride;

1-cyclopropyl-6-fluoro-8-chloro-7-(3-aminopyrrolidin-1-yl)-3-(2-cyano-2-ethoxycarbonylacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-cyano-2-ethoxycarbonylacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2-cyano-2-ethoxycarbonylacetyl)-1,4-dihydro-4-oxoquinoline hydrochloride;

1-cyclopropyl-6-fluoro-8-chloro-7-(3-aminopyrrolidin-1-yl)-3-(2-cyanoacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-cyanoacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2-cyanoacetyl)-1,4-dihydro-4-oxoquinoline hydrochloride;

1-cyclopropyl-6-fluoro-8-chloro-7-(3-aminopyrrolidin-1-yl)-3-(2,2-dicyanoacetyl)-1,4-dihydro-4-oxoquinoline hydrochloride;

1-cyclopropyl-6-fluoro-8-chloro-7-(3-methylaminomethyl-2,5-dihydropyrrol-1-yl)-3-(2-methanesulfonylacetyl)-1,4-dihydro-4-oxoquinoline hydrochloride;

1-cyclopropyl-6-fluoro-8-chloro-7-(3,7-diazabicyclo[3.3.0]oct-1,5-en-3-yl)-3-(2-methanesulfonylacetyl)-1,4-dihydro-4-oxoquinoline hydrochloride;

1-cyclopropyl-6-fluoro-8-chloro-7-(3-aminopyrrolidin-1-yl)-3-(2,2-diacetoacetyl)-1,4-dihydro-4-oxoquinoline hydrochloride;

1-cyclopropyl-6-fluoro-8-methoxy-7-(3-aminopyrrolidin-1-yl)-3-(2-nitroacetyl)-1,4-dihydro-4-oxoquinoline hydrochloride;

1-cyclopropyl-6-fluoro-8-methyl-7-(3-aminopyrrolidin-1-yl)-3-(2-nitroacetyl)-1,4-dihydro-4-oxoquinoline hydrochloride;

1-cyclopropyl-5-methyl-6-fluoro-7-(3-methylpiperazin-1-yl)-3-(2-nitroacetyl)-1,4-dihydro-4-oxoquinoline hydrochloride;

1-cyclopropyl-6-fluoro-8-chloro-7-(3-aminopyrrolidin-1-yl)-3-(2-amido-2-ethoxycarbonylacetyl)-1,4-dihydro-4-oxoquinoline hydrochloride; and 1-cyclopropyl-6-fluoro-8-chloro-7-(3-aminomethylpyrrolidin-1-yl)-3-(2-nitroacetyl)-1,4-dihydro-4-oxoquinoline hydrochloride.

4. An antibacterial composition comprising a compound of formula (I) or its acid addition salt as an active ingredient and pharmaceutically acceptable excipients.

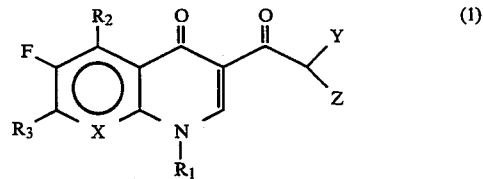

wherein:

$R_1$, $R_2$, $R_3$, X, Y and Z are the same as defined in claim 1.

5. A method of treatment for prophylaxis or therapy of local or systemic bacterial infection comprising administering to the patient a compound of formula (I).

* * * * *

UNITED STATES PATENT AND TRADEMARK OFFICE
CERTIFICATE OF CORRECTION

PATENT NO. : 5,409,933
DATED : April 25, 1995
INVENTOR(S) : Kim, et. al.

It is certified that error appears in the above-indentified patent and that said Letters Patent is hereby corrected as shown below:

```
Title page, col. 2, -- Foreign Application Priority Data should
read--June 9, 1992 [KR] Korea........9929/1992--.
```

Signed and Sealed this

Second Day of January, 1996

Attest:

BRUCE LEHMAN

*Attesting Officer*  *Commissioner of Patents and Trademarks*